US012622722B2

(12) United States Patent
Floyd et al.

(10) Patent No.: US 12,622,722 B2
(45) Date of Patent: May 12, 2026

(54) SURGICAL INSTRUMENT SHEARS

(71) Applicant: Intuitive Surgical Operations, Inc., Sunnyvale, CA (US)

(72) Inventors: Paul Floyd, San Jose, CA (US); Erik Nelson, Durango, CO (US); Matthew Wixey, Rochester, MI (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 186 days.

(21) Appl. No.: 18/683,672

(22) PCT Filed: Aug. 16, 2022

(86) PCT No.: PCT/US2022/040452
§ 371 (c)(1),
(2) Date: Feb. 14, 2024

(87) PCT Pub. No.: WO2023/023045
PCT Pub. Date: Feb. 23, 2023

(65) Prior Publication Data
US 2024/0341799 A1      Oct. 17, 2024

Related U.S. Application Data

(60) Provisional application No. 63/234,662, filed on Aug. 18, 2021.

(51) Int. Cl.
*A61B 17/3201* (2006.01)
*A61B 17/29* (2006.01)

(52) U.S. Cl.
CPC .. *A61B 17/3201* (2013.01); *A61B 2017/2932* (2013.01)

(58) Field of Classification Search
CPC ........ A61B 2017/2932; A61B 17/3201; A61B 17/32
See application file for complete search history.

(56) References Cited

U.S. PATENT DOCUMENTS

| | | |
|---|---|---|
| 5,482,054 A | 1/1996 | Slater et al. |
| 5,490,819 A | 2/1996 | Nicholas et al. |

(Continued)

FOREIGN PATENT DOCUMENTS

| | | |
|---|---|---|
| CA | 2853431 A1 | 5/2013 |
| CN | 1163558 A | 10/1997 |

(Continued)

OTHER PUBLICATIONS

Office Action for EP Application No. EP22777040.1, mailed Feb. 7, 2025, 6 pages.

(Continued)

*Primary Examiner* — Darwin P Erezo
*Assistant Examiner* — Christina C Lauer

(57) ABSTRACT

A medical device includes a blade support, a blade supported by the blade support, and a pin. The blade support includes a bore with an inner portion oriented toward the blade and an outer portion oriented away from the blade. A discontinuity is located at a boundary between the inner and outer portions of the bore. The pin includes a longitudinal axis and a yaw plane is defined perpendicular to the longitudinal axis. A rotational yaw degree of freedom is defined about the longitudinal axis of the pin. The blade support is operable to rotate about the pin in the yaw degree of freedom, contact the pin at the discontinuity of the bore, and tilts away from the yaw plane at the discontinuity of the bore in response to a force applied in a lateral direction.

25 Claims, 26 Drawing Sheets

(56) References Cited

U.S. PATENT DOCUMENTS

| | | | |
|---|---|---|---|
| 5,496,317 | A | 3/1996 | Goble et al. |
| 5,496,347 | A | 3/1996 | Hashiguchi et al. |
| 5,792,165 | A | 8/1998 | Klieman et al. |
| 5,855,583 | A | 1/1999 | Wang et al. |
| 6,273,860 | B1 | 8/2001 | Kostylev et al. |
| 6,623,482 | B2 | 9/2003 | Pendekanti et al. |
| 6,644,532 | B2 | 11/2003 | Green et al. |
| 6,767,349 | B2 | 7/2004 | Ouchi |
| 6,817,974 | B2 | 11/2004 | Cooper et al. |
| 6,840,938 | B1 | 1/2005 | Morley et al. |
| 6,964,662 | B2 | 11/2005 | Kidooka |
| 6,994,708 | B2 | 2/2006 | Manzo |
| 7,083,571 | B2 | 8/2006 | Wang et al. |
| 7,354,439 | B2 | 4/2008 | Kidooka |
| 7,736,356 | B2 | 6/2010 | Cooper et al. |
| 7,824,401 | B2 | 11/2010 | Manzo et al. |
| 7,935,130 | B2 | 5/2011 | Williams |
| 8,568,443 | B1 | 10/2013 | Jackman et al. |
| 9,078,684 | B2 | 7/2015 | Williams |
| 9,204,923 | B2 | 12/2015 | Manzo et al. |
| 9,339,341 | B2 | 5/2016 | Cooper |
| 9,358,031 | B2 | 6/2016 | Manzo |
| 9,456,839 | B2 | 10/2016 | Cooper |
| 9,554,790 | B2 | 1/2017 | Bailey et al. |
| 9,869,339 | B2 * | 1/2018 | Zimmerman ........ A61B 17/062 |
| 10,130,366 | B2 | 11/2018 | Shelton, IV et al. |
| 10,512,481 | B2 | 12/2019 | Cooper |
| 10,524,870 | B2 | 1/2020 | Saraliev et al. |
| 10,932,867 | B2 | 3/2021 | Park |
| 2003/0069477 | A1 | 4/2003 | Raisman et al. |
| 2004/0087940 | A1 | 5/2004 | Jahns et al. |
| 2005/0187547 | A1 | 8/2005 | Sugi |
| 2005/0192598 | A1 | 9/2005 | Johnson et al. |
| 2006/0074415 | A1 | 4/2006 | Scott et al. |
| 2006/0190034 | A1 | 8/2006 | Nishizawa et al. |
| 2007/0208375 | A1 | 9/2007 | Nishizawa et al. |
| 2007/0255109 | A1 | 11/2007 | Stein et al. |
| 2008/0046122 | A1 | 2/2008 | Manzo et al. |
| 2008/0132893 | A1 | 6/2008 | D'Amelio et al. |
| 2008/0167651 | A1 | 7/2008 | Tetzlaff et al. |
| 2009/0088774 | A1 | 4/2009 | Swarup et al. |
| 2009/0209960 | A1 | 8/2009 | Chojin |
| 2010/0198218 | A1 | 8/2010 | Manzo |
| 2012/0010611 | A1 | 1/2012 | Krom et al. |
| 2012/0116433 | A1 | 5/2012 | Houser et al. |
| 2014/0005662 | A1 | 1/2014 | Shelton, IV |
| 2014/0243850 | A1 | 8/2014 | Sadaka |
| 2015/0150635 | A1 | 6/2015 | Kilroy et al. |
| 2015/0280384 | A1 | 10/2015 | Leimbach et al. |
| 2016/0058443 | A1 | 3/2016 | Yates et al. |
| 2016/0143688 | A1 | 5/2016 | Orban, III et al. |
| 2016/0302819 | A1 | 10/2016 | Stulen et al. |
| 2016/0303743 | A1 | 10/2016 | Rockrohr |
| 2017/0007242 | A1 | 1/2017 | Shelton, IV et al. |
| 2018/0116708 | A1 | 5/2018 | Manzo et al. |
| 2019/0374240 | A1 * | 12/2019 | Brodbeck .............. A61B 17/29 |
| 2019/0374297 | A1 | 12/2019 | Wallace et al. |
| 2019/0380800 | A1 | 12/2019 | Jogasaki et al. |
| 2020/0054405 | A1 | 2/2020 | Schuh et al. |
| 2020/0054408 | A1 | 2/2020 | Schuh et al. |
| 2021/0169597 | A1 * | 6/2021 | Abbott ........... A61B 17/320016 |
| 2021/0177534 | A1 | 6/2021 | Park |
| 2022/0226051 | A1 | 7/2022 | Johnson et al. |
| 2024/0016566 | A1 * | 1/2024 | Lazzari ................. A61B 34/71 |
| 2025/0176970 | A1 * | 6/2025 | Sinisi ................. A61B 17/1285 |

FOREIGN PATENT DOCUMENTS

| | | | |
|---|---|---|---|
| JP | H10510169 | A | 10/1998 |
| JP | 2004524923 | A | 8/2004 |
| JP | 2010022696 | A | 2/2010 |
| WO | WO-9610957 | A1 | 4/1996 |
| WO | WO-2015088647 | A1 | 6/2015 |
| WO | WO-2022072732 | A1 | 4/2022 |

OTHER PUBLICATIONS

International Search Report & Written Opinion for PCT Application No. PCT/US2022/040452, mailed Nov. 16, 2022, 10 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

1150

SURGICAL INSTRUMENT SHEARS

CROSS-REFERENCE TO RELATED APPLICATIONS

This application is a U.S. national stage filing under 35 U.S.C. § 371 of International Application No. PCT/US2022/040452, entitled "Surgical Instrument Shears," filed Aug. 16, 2022, which claims benefit of priority to U.S. Provisional Application Ser. No. 63/234,662, entitled "Surgical Instrument Shears," filed Aug. 18, 2021, each of which is incorporated herein by reference in its entirety.

BACKGROUND

The embodiments described herein relate to medical devices, and more specifically to endoscopic tools. More particularly, the embodiments described herein relate to devices that include instrument tools, such as shears, that rotate and tilt about a supporting pin to improve cutting.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of a shaft. During an MIS procedure, the end effector, wrist mechanism, and the distal end of the shaft are inserted into a small incision or a natural orifice of a patient to position the end effector at a work site within the patient's body. The optional wrist mechanism can be used to change the end effector's orientation with reference to the shaft to perform the desired procedure at the work site. Known wrist mechanisms generally provide the desired mechanical degrees of freedom (DOFs) for movement of the end effector. For example, known wrist mechanisms are able to change the pitch and yaw orientation of the end effector with reference to the shaft's longitudinal axis. A wrist may optionally provide a roll DOF for the end effector with reference to the shaft, or an end effector roll DOF may be implemented by rolling the shaft, wrist, and end effector together as a unit. An end effector may optionally have additional mechanical DOFs, such as grip or knife blade motion. In some instances, wrist and end effector mechanical DOFs may be combined to provide various end effector control DOFs. For example, U.S. Pat. No. 5,792,135 (filed May 16, 1997) discloses a mechanism in which wrist and end effector grip mechanical DOFs are combined to provide an end effector yaw control DOF.

To enable the desired movement of the distal wrist mechanism and end effector, known instruments include cables that extend through the shaft of the instrument and that connect the wrist mechanism to a mechanical structure configured to move the cables to operate the wrist mechanism and end effector. For teleoperated systems, the mechanical structure is typically motor driven and is operably coupled to a computer processing system to provide a user interface for a clinical user (e.g., a surgeon) to control the instrument as a whole, as well as the instrument's components and functions.

Patients benefit from continual efforts to improve the effectiveness of MIS methods and devices. For example, reducing the size and/or the operating footprint of the shaft and wrist mechanism can allow for smaller entry incisions and reduced need for space at the surgical site, thereby reducing the negative effects of surgery, such as pain, scarring, and undesirable healing time. But producing small medical devices that implement the clinically desired functions for minimally invasive procedures can be challenging. Specifically, simply reducing the size of known wrist mechanisms by scaling down the components will not result in an effective solution because required component and material properties do not scale at relatively small physical dimensions. For example, efficient implementation of a wrist mechanism can be complicated because the cables must be carefully routed through the wrist mechanism to maintain cable tension throughout the range of motion of the wrist mechanism or end effector and to minimize the interactions (coupling effects) of motion about one rotation axis upon motion about another rotation axis. As another example, pulleys and/or contoured surfaces are generally needed to reduce cable friction, which extends instrument life and permits operation without excessive forces being applied to the cables or other structures in the wrist mechanism. But increased localized forces that may result from smaller structures and cable bend radii (including smaller diameter cables and other wrist and end effector components) can result in undesirable lengthening (e.g., stretch or creep) of the cables during storage and use, reduced cable life, and the like.

Further, the wrist mechanism generally provides specific degrees of freedom for movement of the end effector. For example, for forceps or other grasping tools, the wrist may be able to change the end effector pitch, yaw, and grip orientations with reference to the instrument shaft. More degrees of freedom could be implemented through the wrist but would require additional actuation members (e.g., cables) in the wrist and shaft, and these additional members compete for the limited space that exists given the size restrictions required by MIS applications. Components needed to actuate other degrees of freedom, such as end effector roll or insertion/withdrawal through movement of the main tube, also compete for space at or in the shaft of the device.

Some known end effectors employ a pair of opposing blades, which function as shears to perform cutting operations on tissue or structure during a procedure. As the blades actuate from a first orientation (e.g., blades in a fully open orientation) to a second orientation (e.g., blades in a fully or partially closed orientation) the cutting location translates along the cutting surfaces of the blades outwardly away from the axis of rotation. This enables the blades to redirect the cutting force to a smaller cutting location and allow the cutting surfaces to cut an object while minimizing the force that pushes the object outwardly away from the cutting surfaces. Some known blades are designed to produce a slight interference fit between the cutting surfaces at the contact location. Thus, the blades can deform slightly during the cutting operation. In order to permit the appropriate deformation and enable the blades to return back to their original shape (i.e., shape of the blades prior to the blades being moved from the first orientation to the second orientation), known blades are often machined from a suitable material with a sufficient thickness to maintain the desired rigidity. However, the thickness and associated machining process for producing such known rigid blades increases the overall production time and cost.

Some known blades include longer blade lengths to provide sufficient deformation to redirect the cutting force to the smaller cutting location. This in turn causes the beginning cutting point (i.e., at or near the first orientation) to be spaced further away from the rotational axis of the machined blades.

Thus, a need exists for improved medical devices, including improved end effectors that reduce manufacturing time and cost, while providing good cutting performance. Furthermore, a need exists for reducing the overall length of the cutting blades and shifting the beginning cutting point closer to the rotational axis of the end effectors in order to make the end effector more compact and more maneuverable at the work site.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, a medical device includes a blade support, a blade supported by the blade support, and a pin. The blade support includes a bore with an inner portion oriented toward the blade and an outer portion oriented away from the blade. A discontinuity is located at a boundary between the inner and outer portions of the bore. The pin extends through the bore of the blade support, and the pin includes a first end and a second end opposite the first end. The pin includes a longitudinal axis defined between the first and second ends of the pin, and a yaw plane is defined perpendicular to the longitudinal axis. A lateral direction is defined as a direction away from the yaw plane. A rotational yaw degree of freedom is defined about the longitudinal axis of the pin. The blade support is operable to rotate about the pin in the yaw degree of freedom, contact the pin at the discontinuity of the bore, and tilts away from the yaw plane at the discontinuity of the bore in response to a force applied in the lateral direction.

Other medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

DETAILED DESCRIPTION

Figure 1:
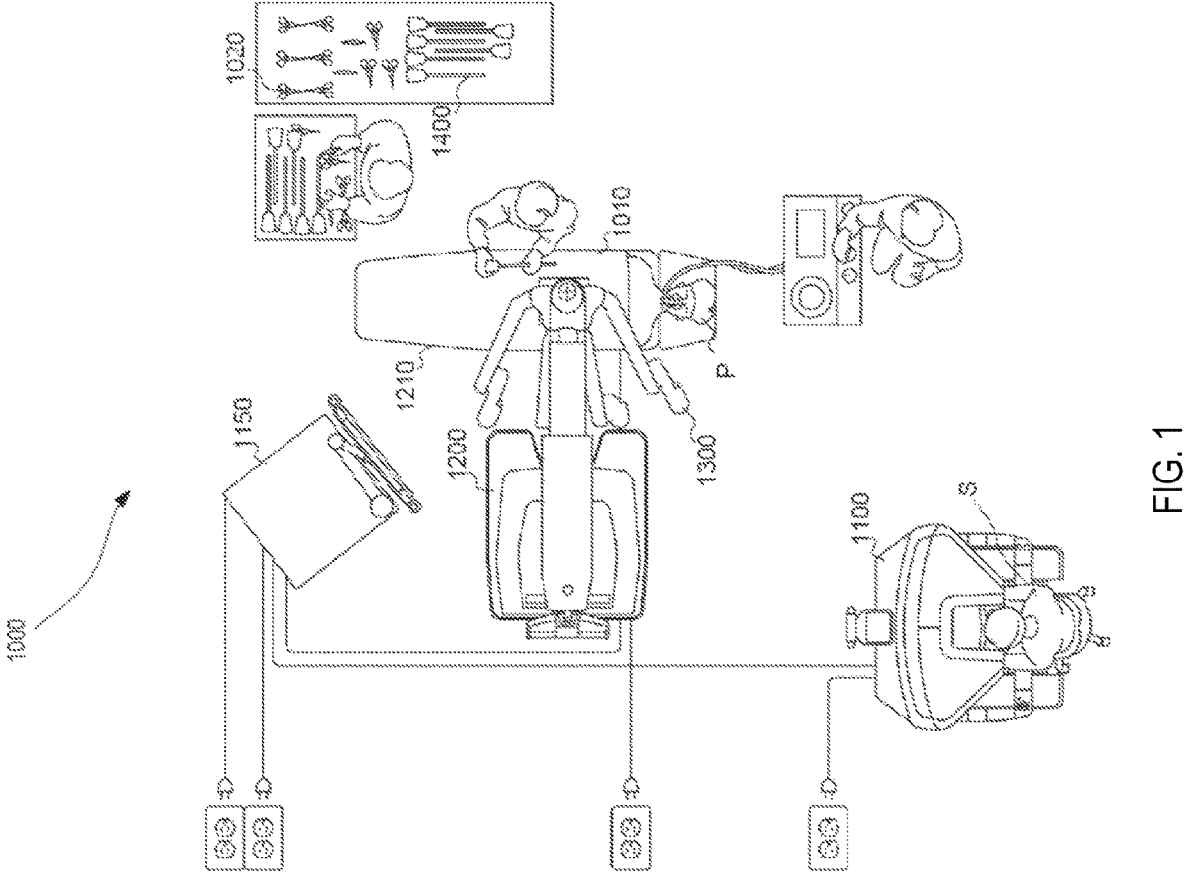
FIG. 1 is a plan view of a minimally invasive teleoperated medical system according to an embodiment being used to perform a medical procedure such as surgery.

The embodiments described herein can advantageously be used in a wide variety of cutting, manipulating, and electrocautery operations associated with minimally invasive surgery. In some embodiments, an end effector of the medical device can move with reference to the main body of the instrument in three mechanical DOFs, e.g., pitch, yaw;

and roll (shaft roll). There may also be one or more mechanical DOFs in the end effector itself, e.g., two jaws, each rotating with reference to a clevis (2 DOFs) and a distal clevis that rotates with reference to a proximal clevis (one DOF).

The medical devices of the present application enable motion in three degrees of freedom (e.g., about a pitch axis, a yaw axis, and a grip axis) using only four cables, thereby reducing the total number of cables required, reducing the space required within the shaft and wrist, reducing overall cost, and enables further miniaturization of the wrist and shaft assemblies to promote MIS procedures. Moreover, the instruments described herein include one or more cables (which function as tension members) that are made of a polymer material and that can be secured to a capstan of the proximal end mechanism without the need for a retention element or other securing feature. In some embodiments, the capstans are configured with grooves, and a cable is wrapped about a capstan and disposed at least partially within the grooves such that a first wrap portion of the cable crosses over a second wrap portion of the cable. The cross-over configuration assists in securing the cables to the capstans. The polymer material of the cable or a coating applied to the surface of the cable also provides sufficient friction to further assist in maintaining the cable secured to the capstan without the need for any additional mechanical features for securing the cable to the capstan (e.g., placing cable crimps within a guide slot, securing the cable to the capstan with an adhesive, or the like).

Additionally, the instruments described herein have end effectors having cutting blades that are thinner and shorter to improve maneuverability while minimizing manufacturing time and cost. The instruments described herein also have blade supports that provide a level of compliance for opposing blades to temporarily deform and return back to their initial shape and geometry. The temporary deformation supported by the blade supports enable the thinner and shorter blades to effectively redirect the cutting force to a smaller contact patch. The blade supports also provide a blade gap behind and ahead of the cutting to enable a clean cut and prevent clogging of the object to be cut.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

As used in this specification and the appended claims, the word "distal" refers to direction towards a work site, and the word "proximal" refers to a direction away from the work site. Thus, for example, the end of a medical device that is closest to the target tissue would be the distal end of the medical device, and the end opposite the distal end (i.e., the end manipulated by the user or coupled to the actuation shaft) would be the proximal end of the medical device.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below: A device may be otherwise oriented (e.g., rotated 90 degrees or at other orientations) and the spatially relative descriptors used herein interpreted accordingly. Likewise, descriptions of movement along (translation) and around (rotation) various axes includes various spatial positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, medical instrument, and variants thereof, can be interchangeably used.

Aspects of the invention are described primarily in terms of an implementation using a da Vinci® surgical system, commercialized by Intuitive Surgical, Inc. of Sunnyvale, California. Examples of such surgical systems are the da Vinci Xi® surgical system (Model IS4000), da Vinci X® Surgical System (Model IS4200), and the da Vinci Si® surgical system (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® surgical systems (e.g., the Model IS4000, the Model IS3000, the Model IS2000, the Model IS1200, the Model SP1099) are merely presented as examples, and they are not to be considered as limiting the scope of the inventive aspects disclosed herein. As applicable, inventive aspects may be embodied and implemented in both relatively smaller, hand-held, hand-operated devices that are not mechanically grounded in a world reference frame and relatively larger systems that have additional mechanical support that is grounded in a world reference frame.

FIG. 1 is a plan view illustration of a teleoperated surgical system 1000 that operates with at least partial computer assistance (a "telesurgical system"). Both telesurgical system 1000 and its components are considered medical devices. Telesurgical system 1000 is a Minimally Invasive Robotic Surgical (MIRS) system used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot) and an optional auxiliary equipment unit 1150. The manipulator unit 1200 can include an arm assembly 1300 and a surgical instrument tool assembly removably coupled to the arm assembly. The manipulator unit 1200 can manipulate at least one removably coupled instrument 1400 through a minimally invasive incision in the body or natural orifice of the patient P while the surgeon S views the surgical site and controls movement of the instrument 1400 through control unit 1100. An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of instruments 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
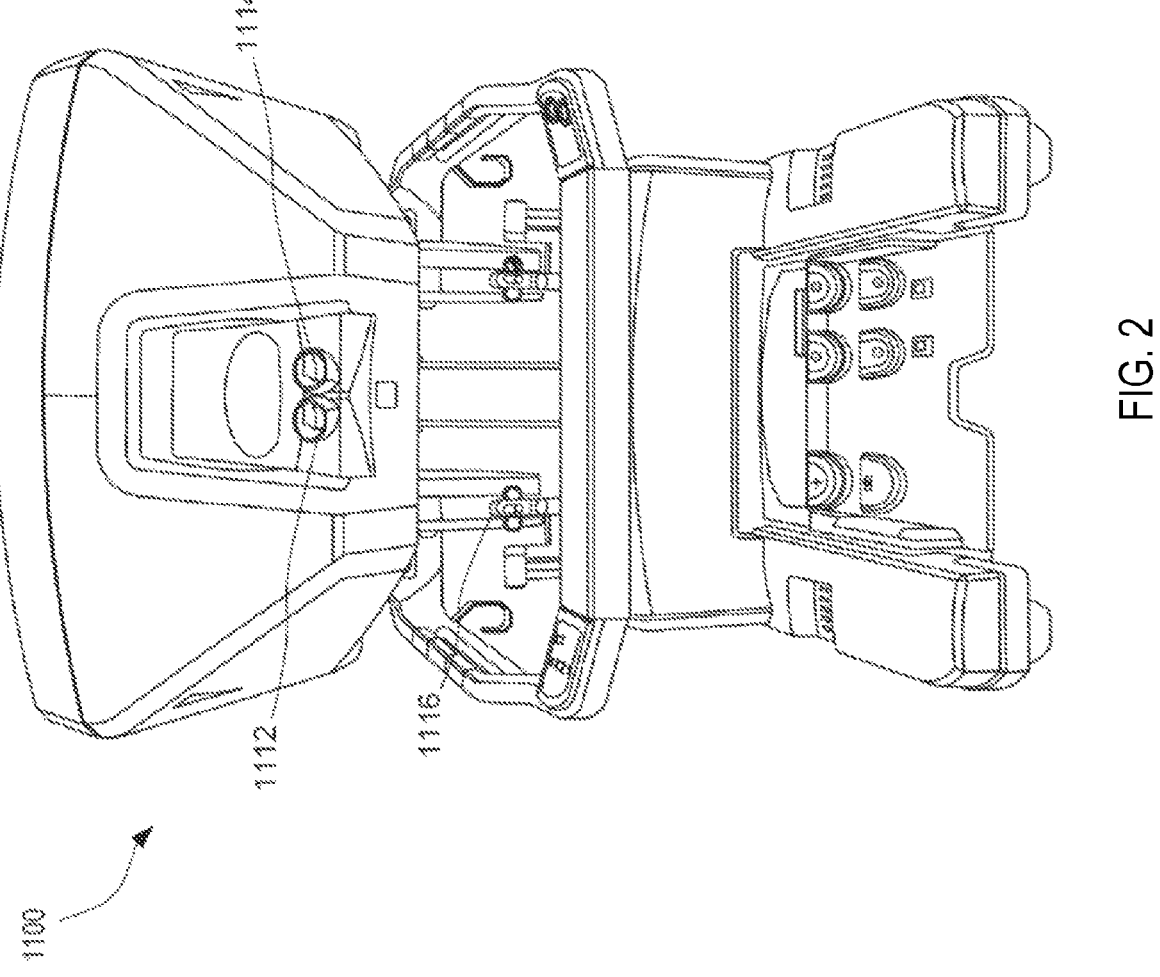
FIG. 2 is a perspective view of an optional auxiliary unit of the minimally invasive teleoperated surgery system shown in FIG. 1.

FIG. 2 is a perspective view of the control unit 1100. The user control unit 1100 includes a left eye display 1112 and a right eye display 1114 for presenting the surgeon S with a coordinated stereoscopic view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, strain, or tactile feedback sensors (not shown) or any combination of such sensations, from the instruments 1400 back to the surgeon's hand or hands through the one or more input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments, however, the user control unit 1100 and the surgeon S can be in a different room, a completely different building, or other location remote from the patient, allowing for remote surgical procedures.

Figure 3:
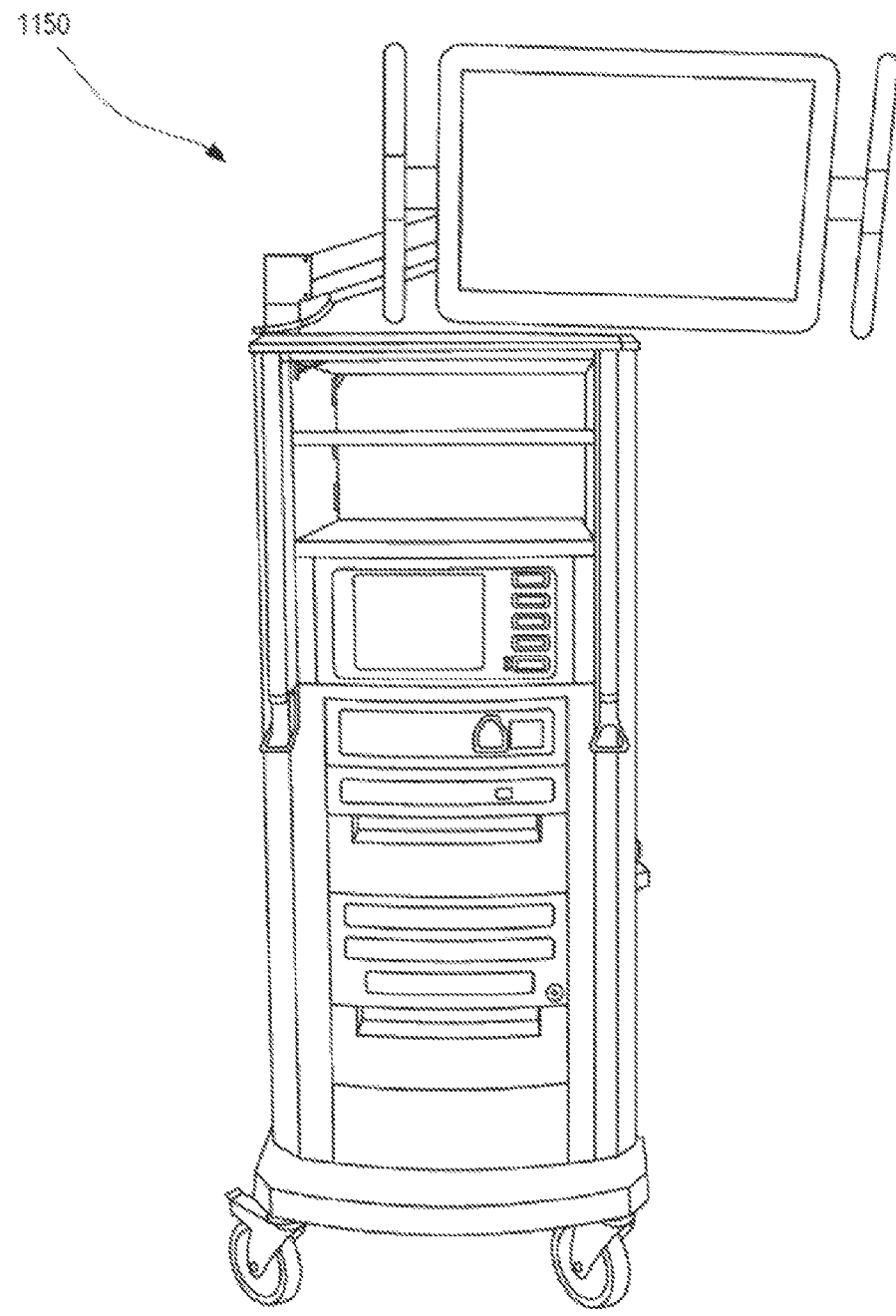
FIG. 3 is a perspective view of a user control console of the minimally invasive teleoperated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally (e.g., on the unit 1150 itself as shown, on a wall-mounted display) and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
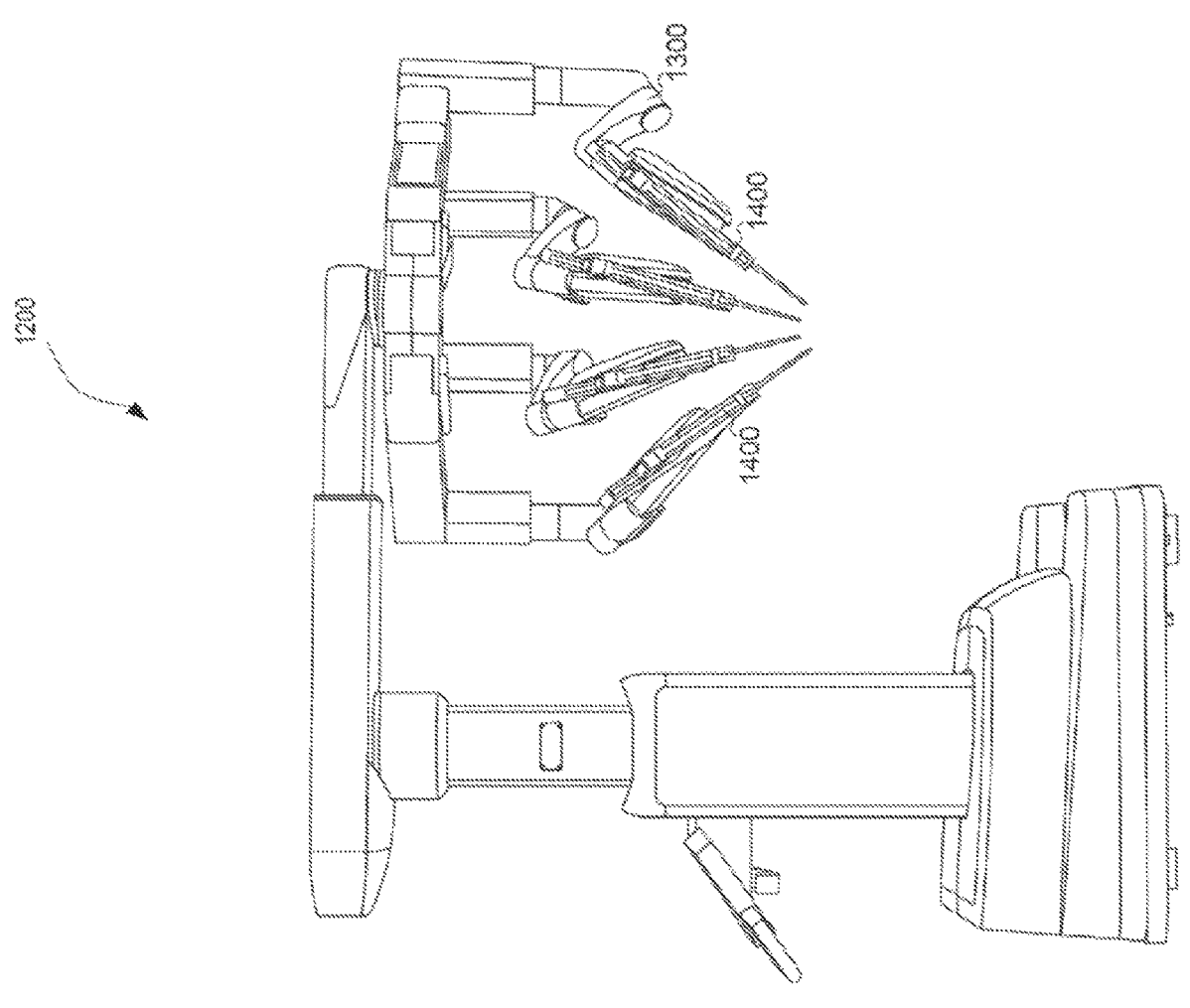
FIG. 4 is a front view of a manipulator unit, including a plurality of instruments, of the minimally invasive teleoperated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having one or more mechanical joints. Moreover, the instruments 1400 and the imaging device are positioned and manipulated through incisions or natural orifices in the patient P in a manner such that a center of motion remote from the manipulator and typically located at a position along the instrument shaft is maintained at the incision or orifice by either kinematic mechanical or software constraints. In this manner, the incision size can be minimized.

Figure 5:
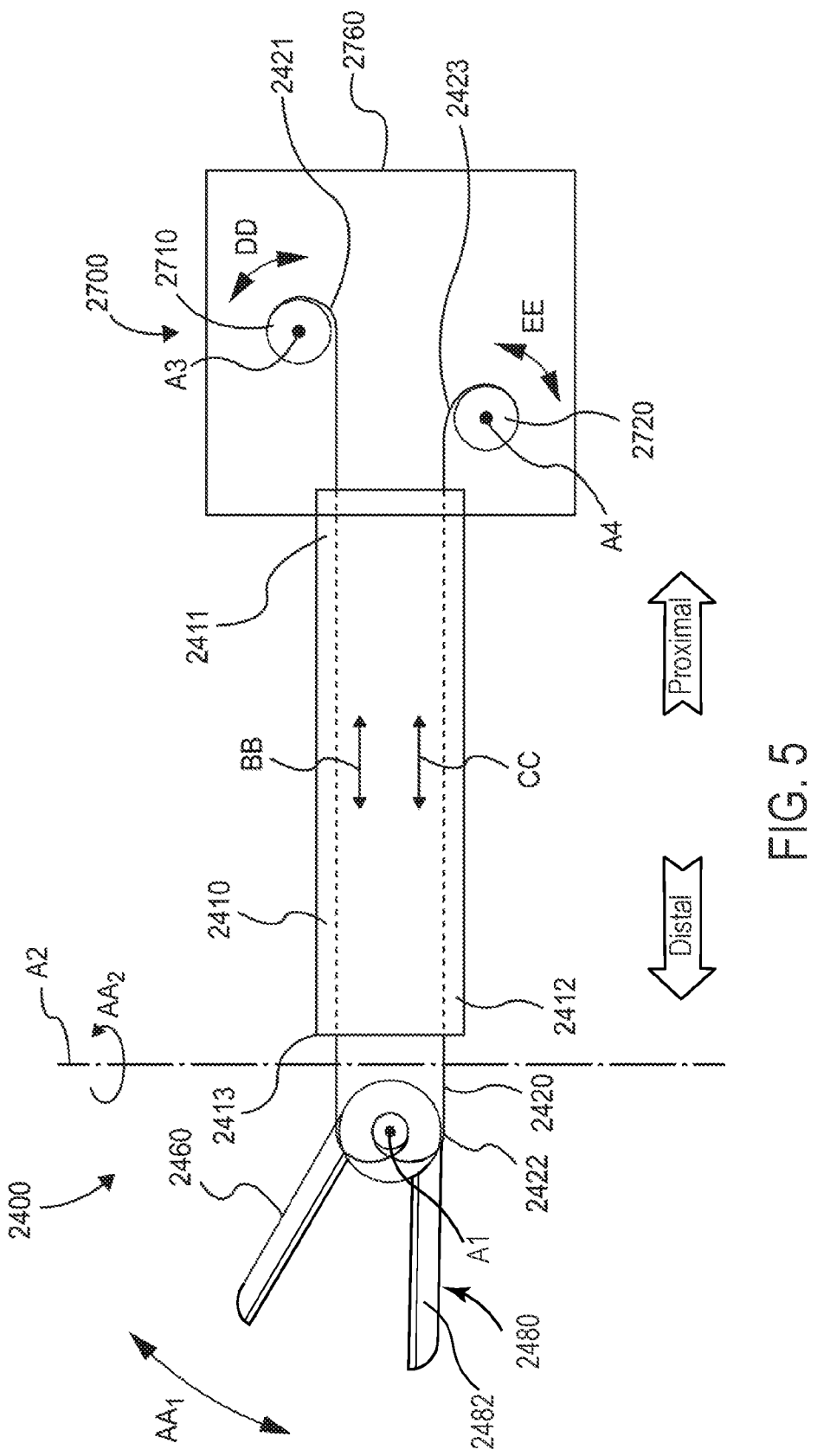
FIG. 5 is a diagrammatic illustration of a portion of a medical device according to an embodiment, illustrating a cutting blade in a first orientation.

FIG. 5 is a schematic illustration of a portion of a medical device 2400 according to an embodiment. The instrument 2400 includes a shaft 2410, a cable 2420 (which acts as a first tension member), an end effector 2460, and a mechanical structure 2700. In many embodiments, mechanical structure 2700 functions to receive one or more motor input forces or torques and mechanically transmit the received forces or torques to move an associated one or more components in instrument 2400. For example, one or more electric motors in manipulator unit 1200 provide an input to mechanical structure 2700, which in turn transmits the input to control an instrument 2400 component. In some optional embodiments, the mechanical structure 2700 includes one or more motors used to control an instrument 2400 component. In some embodiments, the mechanical structure 2700 (and any of the mechanical structures described herein) can include one or more drive motors to produce the force or torque to move the components of the medical device 2400. In other embodiments, mechanical structure 2700) (and any of the mechanical structures described herein) is devoid of any motors and transmits force or torque from outside the medical device to one or more of the medical device's components. For example, in some embodiments, the mechanical structure 2700) (and any of the mechanical structures described herein) is coupled to a manipulator unit that includes one or more motors that drive an instrument component. The cable 2420 includes a first proximal portion 2421, a second proximal portion 2423 and a distal portion 2422. The first proximal portion 2421 and the second proximal portion 2423 are each coupled to the mechanical structure 2700, and the distal portion 2422 is coupled to the end effector 2460. The shaft 2410 includes a proximal end portion 2411 and a distal end portion 2412 and defines a passageway 2413 that extends lengthwise through the shaft between the proximal and distal end portions.

The end effector 2460 is rotatably coupled to the distal end portion 2412 of the shaft 2410 and includes a first tool member 2462 and a second tool member 2482. In some embodiments, the first tool member 2462 is rotatably supported by a pin 2490) and the second tool member 2482 is fixed relative to the pin 2490). In some embodiments, the first tool member 2462 is a rotatable blade and the second tool member 2482 is a fixed blade or support structure for probing, holding, or bracing an object to be cut. In other embodiments, the second tool member 2482 can rotate relative to the pin 2490.

The instrument 2400 is configured such that movement of the first proximal portion 2421 and the second proximal portion 2423 of the cable 2420 produces movement of the first tool member 2462 about a first axis of rotation $A_1$ (which functions as the yaw axis: the term yaw is arbitrary), in a direction of arrows $AA_1$. In some embodiments, the medical device 2400) can include a wrist assembly including one or more links (not shown in FIG. 5) that couple the end effector 2460 to the distal end portion 2412 of the shaft 2410. In such an embodiment, movement of the first proximal portion 2421 and the second proximal portion 2423 of the cable 2420) can also produce movement of the wrist assembly about a second axis of rotation (not shown in FIG. 5, but which functions as the pitch axis: the term pitch is arbitrary) or both movement of the wrist assembly and the end effector 2460. An embodiment with a wrist assembly is described and shown in FIGS. 21-36 of International Application No. PCT/US2021/017840 (filed Feb. 12, 2021), entitled "Devices and Methods of Coupling a Cable to a Medical Device," which is incorporated herein by reference in its entirety.

The first tool member 2462 includes a proximal end portion 2466 and a distal end portion 2467. The first tool member 2462 further includes a contact portion 2464 (which functions as a cutting surface). The proximal end portion 2466 of the first tool member 2462 is coupled to a blade support 2860. The second tool member 2482 includes a contact portion 2484, a proximal end portion 2486 and a distal end portion 2487. The contact portion 2464 is configured to engage the contact portion 2484 to cut a target tissue positioned between the contact portions 2464, 2484. In some embodiments, the contact portions 2464, 2484 can be energized portions of the tool member that is used for cauterization or electrosurgical procedures.

The end effector 2460 is operatively coupled to the mechanical structure 2700 such that the first tool member 2462 rotates relative to shaft 2410 about the first axis of rotation $A_1$ in the direction of the arrow $AA_1$. In this manner, the contact portion 2464 of the first tool member 2462 can be actuated to engage different points of the contact portion 2484 of the second tool member 2482 to cut a length of the target tissue placed between the first tool member 2462 and the second tool member 2482.

The mechanical structure 2700 optionally includes a chassis 2760, a first capstan 2710, and a second capstan 2720. The chassis 2760 provides the structural support for mounting or supporting and aligning the components of the mechanical structure 2700. For example, openings, protrusions, mounting brackets and the like can be defined in or on chassis 2760. In some embodiments, the chassis 2760 can include multiple portions, such as an upper chassis and a lower chassis. In some embodiments, a housing can optionally enclose at least a portion of the chassis 2760. The optional first capstan 2710 is mounted to the mechanical structure 2700 (e.g., within the housing 2760) via a first capstan support member (not shown). For example, the first capstan support member can be a mount, shaft, or any other suitable support structure to secure the first capstan 2710 to the mechanical structure 2700.

The optional second capstan 2720 is mounted to the mechanical structure 2700 (e.g., within the housing 2760) via a second capstan support member (not shown). For example, the second capstan support member can be a mount, shaft, or any other suitable support structure to secure the second capstan 2720 to the mechanical structure 2700. The first capstan 2710 can be operable to be rotated about an axis A3 in a direction DD, as shown in FIG. 5. The second capstan 2720 can be operable to be rotated about an axis A4 parallel to the axis A3.

The cable 2420 is routed from the mechanical structure 2700 to the end effector 2460 and then back to mechanical structure 2700, and each individual end of the cable is coupled to either the first capstan 2710 or the second capstan 2720 of the mechanical structure 2700. More specifically, the first proximal portion 2421 of the cable 2420 is coupled to the first capstan 2710 of the mechanical structure 2700, the cable 2420 extends from the first capstan 2710 along the shaft 2410, and the distal portion 2422 of the cable 2410 is coupled to the end effector 2460, as described in more detail herein. Although the cable 2420 is shown extending within an interior passageway of the shaft 2410 in FIG. 5, in other embodiments, the cable 2420) can be routed exterior to the shaft 2410. The cable 2420 extends from the end effector 2460 along the shaft 2410 and the second proximal portion 2423 is coupled to the second capstan 2720 of the mechanical structure 2700. In other words, the two ends of a single cable (e.g., 2420) are coupled to and actuated by two separate capstans of the mechanical structure 2700.

More specifically, the two ends of the cable 2420 that are associated with opposing directions of a single degree of freedom are connected to two independent drive capstans 2710 and 2720. This arrangement, which is generally referred to as an antagonist drive system, allows for independent control of the movement of (e.g., pulling in or paying out) each of the ends of the cable 2420. The mechanical structure 2700 produces movement of the cable 2420, which operates to produce the desired articulation movements (pitch, yaw, or grip) at the end effector 2460. Accordingly, as described herein, the mechanical structure 2700 includes components and controls to move a first portion of the cable 2420 via the first capstan 2710 in a first direction (e.g., a proximal direction) and to move a second portion of the cable 2420 via the second capstan 2720 in a second opposite direction (e.g., a distal direction). The mechanical structure 2700 can also move both the first portion of the cable 2420 and the second portion of the cable 2420 in the same direction. In this manner, the mechanical structure 2700 can maintain the desired tension within the cables to produce the desired movements at the end effector 2460.

In other embodiments, however, any of the medical devices described herein can have the two ends of the cable wrapped about a single capstan. This alternative arrangement, which is generally referred to as a self-antagonist drive system, operates the two ends of the cable using a single drive motor. In yet other embodiments, mechanical structure 2700 (and any of the mechanical structures described herein) need not include capstans to move the cable, but can include any other suitable mechanism for moving the cable (e.g., a push-pull mechanism, a movable rack, or the like).

In addition, in some alternative embodiments, the cable 2420) includes two cable segments, with each cable segment having a distal end portion that is coupled to the end effector 2460 and a proximal end portion wrapped about a capstan—either separate capstans as in the antagonist drive arrangement or a single common capstan in the self-antagonist drive arrangement. Descriptions herein referring to the use of a single cable 2420 incorporate the similar use of two separate cable segments.

With the cable 2420 coupled to the mechanical structure 2700 and to the end effector 2460), rotational movement produced by the first capstan 2710) causes the first proximal portion 2421 of the cable 2420 to move in a direction BB (e.g., proximally or distally depending on the direction of rotation), as shown in FIG. 5. Similarly, rotational movement produced by the second capstan 2720) causes the second proximal portion 2423 of the cable 2420 to move in the direction CC (e.g., proximally or distally depending on the direction of rotation), as shown in FIG. 5. Said another way, the first capstan 2710 can be operable to produce rotational movement about the axis A3, and the second capstan 2720 can similarly be operable to produce rotational movement about an axis A4 parallel to the axis A3. Thus, the first capstan 2710) can rotate in the direction of arrows DD and the second capstan 2720 can rotate in the direction of arrows EE in FIG. 5. For example, when the first capstan 2710 rotates about the axis A3 in a first direction (clockwise or counter-clockwise), the second capstan 2720 rotates about the axis A4 in either the same or the opposite direction (clockwise or counter-clockwise). Thus, as one of the capstans 2710, 2720 pays out the cable 2420, the other of the capstans 2710, 2720 pays in the cable 2420. Depending on how the cables are routed to the various capstans, it doesn't matter what direction each of the individual capstans rotates as long as the desired individual cable pay-in or pay-out is performed to perform the desired end effector motion-grip, yaw, or pitch-either alone or in combination.

With each of the ends of the cable 2420 coupled to a separate capstan, the movement of a first portion of the cable 2420 can be directly controlled by one capstan (e.g., first capstan 2710) and movement of a second portion of the cable 2420 can be directly controlled by the other capstan (e.g., second capstan 2720). Thus, the control of motion of the end effector 2460) in one direction is controlled by one capstan, and the control of motion of the end effector 2460) in the other direction is controlled by the other capstan. In this antagonist system, however, when the first capstan 2710 is controlling motion (i.e., applying tension to pull in the first proximal portion 2421 of the cable 2420), the second proximal portion 2423 of the cable is also under tension applied by the second capstan 2720. Maintaining tension applied by the non-driving capstan (i.e., the second capstan 2720) allows the non-driving capstan to immediately function as the driving capstan with no hysteresis in end effector control. The differing levels of tension applied by each capstan can also lead to improved control of the overall movement of the cable. Thus, better control of the overall movement of the end effector 2460 can be achieved. For example, accurate rotation in yaw around axis A$_1$ can be controlled. The first capstan 2710 can be actuated to produce a rotational movement about the axis A3 in the direction of the arrow DD such that the first proximal portion 2421 of the cable is moved in a first direction along arrows BB. Simultaneously, the second capstan 2720 can be actuated to produce rotational movement about an axis parallel to the axis A3 in an opposite direction as the first capstan 2710 such that the second proximal end portion 2723 of the cable 2420 is moved in an opposite direction as the first proximal portion 2421 along arrows CC. Thus, the opposite movement of the first proximal portion 2421 and the second proximal portion 2423 causes the end effector 2460 to rotate (via the cable 2420) connection to the end effector 2460) about the rotational axis A$_1$ (e.g., yaw movement).

In a similar way, accurate rotation in pitch around a second axis A$_2$ (e.g., pitch; orthogonal to the yaw axis A$_1$ described above) can be controlled. As described above, the first capstan 2710 can be actuated to produce a rotational movement about the axis A3 in the direction of the arrow DD, while simultaneously the second capstan 2720 can be actuated to produce rotational movement about the axis A4 parallel to the axis A3 in the direction of the arrow EE such that the first proximal portion 2421 of the cable and the second proximal portion 2423 of the cable 2420 are moved together in the same direction (along arrows BB and CC, respectively). The movement of the first proximal portion 2421 and the second proximal portion 2423 in the same direction causes the end effector 2460 (or a wrist mechanism) to rotate (via the cable 2420) connection to the end effector 2460) about a second rotation axis A$_2$ in the direction of arrow AA$_2$ (e.g., pitch movement). Persons of skill in the art will understand that this action controls rotation around axis A$_2$ in a first direction, and a similar action by an additional cable (or cable segments) (not shown) controls rotation around axis A$_2$ in a second direction opposite the first direction. Thus, an antagonistic control relationship between the cable portions 2420 acting together and the additional cable is used to accurately control end effector rotation in pitch. Alternatively, a resiliency such as a spring may be used to act against cable portions 2420 to urge rotation around axis A$_2$ in a direction opposite to the direction urged by cable portions 2420. Thus, the combination of the first capstan 2710, the second capstan 2720, and the single cable 2420 are operable to control the end effector 2460 of instrument 2400 in at least 2 DOFs (e.g., pitch and yaw).

The cable 2420, and any of the cables described herein can be made from any suitable materials. For example, in some embodiments, any of the cables described herein can be formed from an ultra-high molecular weight polyethylene (UHMWPE) fiber. In some embodiments, any of the cables described herein can be constructed from a single monofilament. In other embodiments, any of the cables described herein can be constructed from multiple cofilament strands, laid or woven (or both), or thermally fused, or otherwise combined to form the cable. In some embodiments, the cable 2420 or any of the cables described herein can include an optional outer sheath, coating, or other surface treatment to increase the frictional characteristics of the cable. Such increased frictional characteristics help facilitate having the cable 2420 wrapped to the capstan without slipping and without the need for an additional retention feature.

In some embodiments, the cable 2420) and any of the cables described herein can be made from a material having suitable temperature characteristics for use with cauterizing instruments. For example, such materials include liquid crystal polymer (LCP), aramid, para-aramid, and polybenzobisoxazole fiber (PBO). Such materials can provide frictional characteristics that increase the ability for friction coupling and improve holding ability, for example for coupling the cable 2420 to the capstan 2710 and end effector 2460. Such ability can also improve slip characteristics (e.g., help prevent the cable from slipping) during operation of the medical device. Such materials may or may not need a coating or other surface treatment to increase the frictional characteristic.

FIGS. 6A-7B show an enlarged portion of the end effector 2460 of the medical device 2400. The first tool member 2462 (which functions as a blade) is mounted to a blade support 2860. The blade support 2860 includes a bore 2861 having an inner portion 2862 and an outer portion 2863. The inner portion 2862 is oriented towards (or is closer to) the blade 2462 and the outer portion 2863 is oriented away from (or is further away from) the blade 2462. The bore 2861 has a discontinuity 2864 between the inner portion 2862 and the outer portion 2863 where the bore 2861 transitions from one cross-sectional area to another cross-sectional area along a length of the bore 2861. As described herein, the discontinuity 2864 (or any of the discontinuities described herein) can be formed by changing the cross-sectional area of bore 2861 along its length.

Figures 6A, 6B:
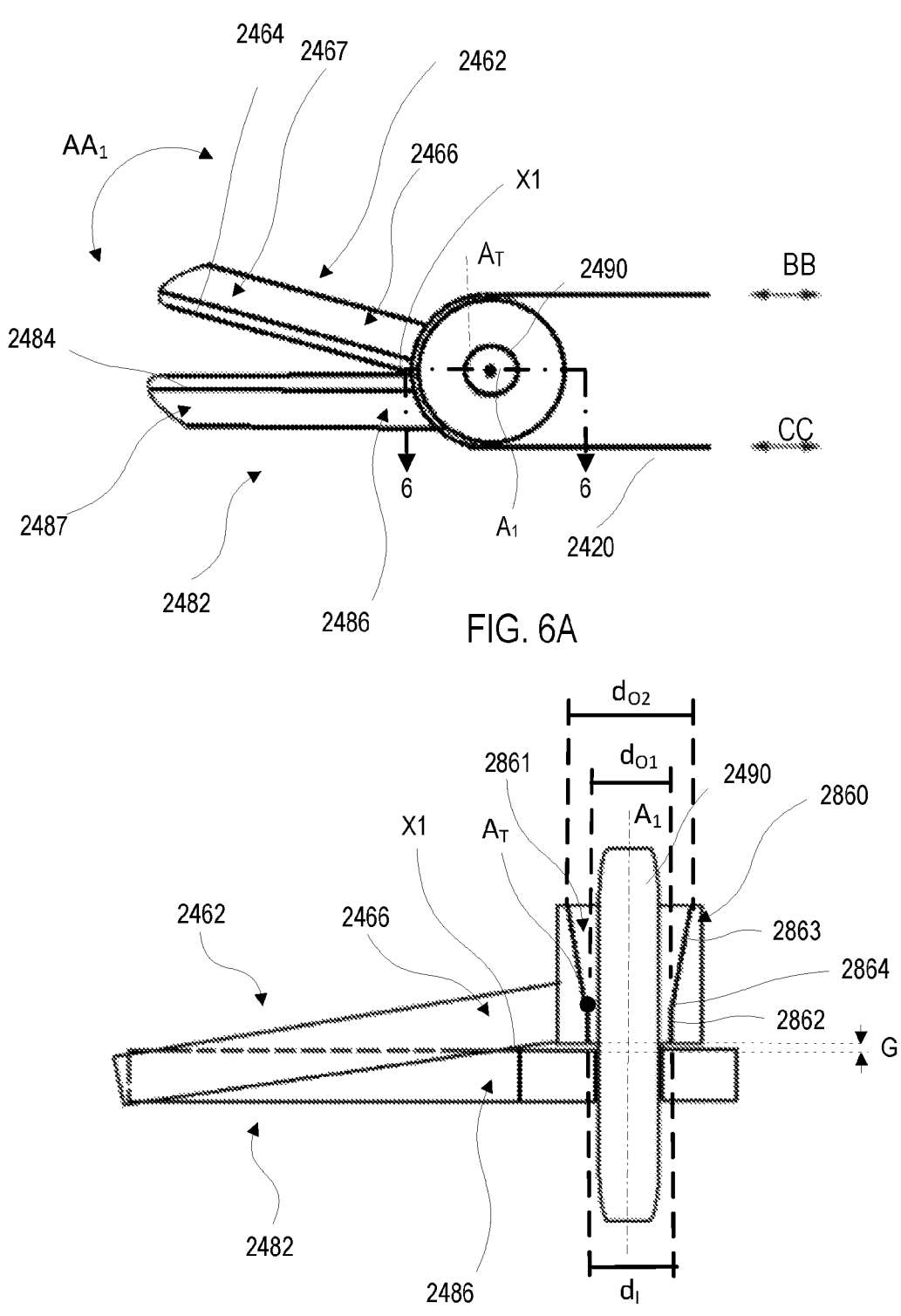
FIG. 6A is a diagrammatic illustration of a portion of the medical device shown in FIG. 5, illustrating the cutting blade in a first orientation.
FIG. 6B is a partial cross sectional view of the portion of the medical device of FIG. 6A taken at line 6-6.
Figure 7A:
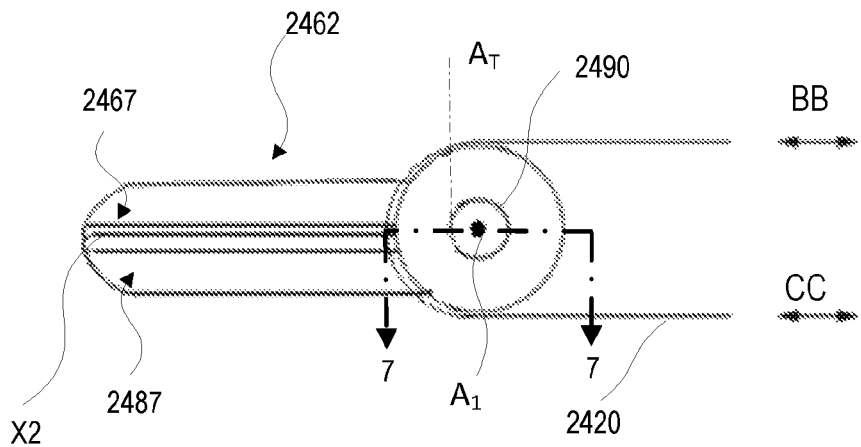
FIG. 7A is a diagrammatic illustration of the portion of the medical device in FIG. 6A illustrating the cutting blade in a second orientation.
Figure 7B:
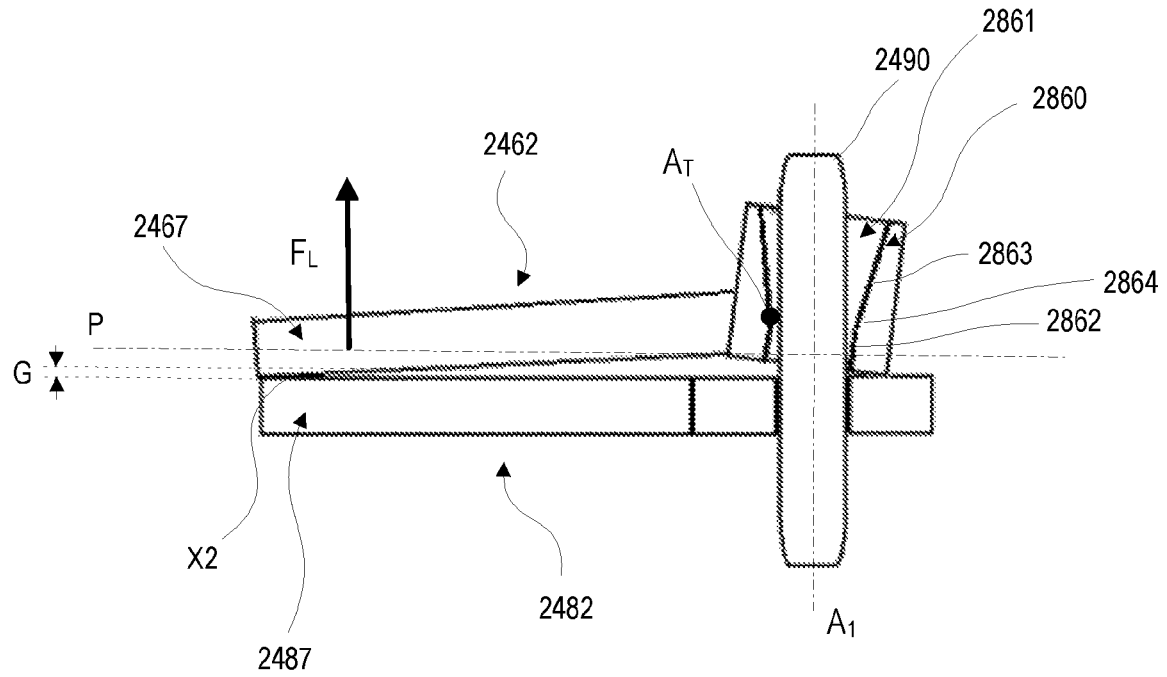
FIG. 7B is a partial cross sectional view of the portion of the medical device of FIG. 7A taken at line 7-7.

A discontinuity can be formed in a variety of different manners. In this example, the inner portion 2862 of the bore 2861 can be provided with at least one cross-sectional area (shape and/or size) different from that of the outer portion 2863 of the bore 2861. As shown in FIGS. 6B and 7B, the inner portion 2862 includes a cylindrical inner surface defined by a diameter $d_I$. The outer portion 2863 includes a truncated conical inner surface defined by a minor diameter $d_{O1}$ and a major diameter $d_{O2}$. The conical inner surface of the outer portion 2863 extends from a minor diameter $d_{O1}$ to a major diameter $d_{O2}$ in a direction away from the inner portion 2862. In some embodiments, the minor diameter $d_{O1}$ of the outer portion 2863 is greater than or equal to the diameter $d_I$ of the inner portion 2862. In this manner, the inner portion 2862 has a constant inner diameter and the outer portion 2863 is tapered, and the discontinuity 2864 is formed at the interface between the inner portion 2862 and the outer portion 2863. In other embodiments, however, the inner portion 2862 can be tapered (e.g., with a major diameter oriented towards (or is closer to) the blade 2462 and a minor oriented away from (or is further away from) the blade 2462, and/or the outer portion 2863 can have a constant inner diameter. By including the discontinuity 2864, the blade support 2860 and therefore the blade 2462 can rotate (tilt) relative to the pin 2490 about a tilt axis $A_T$ as described below.

Although the discontinuity 2864 is shown as being formed at a sharp transition (i.e., step transition) between the inner portion 2862 and the outer portion 2863, in other embodiments, the discontinuity can be formed by a radiused (or smooth) transition between the changed cross-sectional area. The radius transition can have either a convex or concave curvature facing towards the outer portion 2863. In yet other embodiments, the discontinuity can be formed by a ramped (or chamfered) transition between the changed cross-sectional area. The discontinuity 2864 serves as fulcrum about which the blade support 2860 can tilt on an outer circumferential surface of the pin 2490.

The pin 2490 extends through the bore 2861 of the blade support 2860. The first tool member 2462 is coupled to the blade support 2860 and the blade support 2860 is rotatable about the pin 2490 in a yaw degree of freedom. In other words, the blade support 2860 is rotatable about the yaw axis $A_1$ described above. A yaw plane P is defined perpendicular to a longitudinal axis of the pin 2490. The blade support 2860 is operable to tilt at the discontinuity 2864 of the bore 2861 in a lateral direction away from the yaw plane P. Stated in another manner, the blade support 2860 tilts about the tilt axis $A_T$ relative to the pin 2490.

As the first tool member 2462 is rotated in the counter-clockwise direction illustrated by the arrow $AA_1$, the proximal end portion 2466 of the first tool member 2462 begin to contact and interfere with the proximal end portion 2486 of the second tool member 2482. At this first cut point X1, any object positioned between the first tool member 2462 and the second tool member 2482 will begin to be cut. From the first cut point X1, further rotation of the first tool member 2462 will cause a lateral force to be applied on the first tool member 2462, which will in turn cause the blade support 2860 to begin tilting about the tilt axis $A_T$. In particular, as the first tool member 2462 is further rotated in the counter-clockwise direction illustrated by the arrow $AA_1$, the distal end portion 2467 of the first tool member 2462 contacts and interferes with the distal end portion 2487 of the second tool member 2482 at a second cut point X2. The interference between the first tool member 2462 and the second tool member 2482 applies a lateral force $F_L$, which in turn causes the blade support 2860 to further tilt about the tilt axis $A_T$.

Although the first tool member 2462 and the second tool member 2482 are shown as extending linearly, in some embodiments, one or more of the first tool member 2462 and the second tool member 2482 can have a curvilinear geometry. Additionally, although the first tool member 2462 shown in FIG. 7B is shown as maintaining a linear geometry, in some embodiments, the lateral force $F_L$ may cause the first tool member 2462 to temporarily flex and deform away from the second tool member 2482.

As generally shown in FIGS. 6B and 7B, the first tool member 2462 and the second tool member 2482 are non-parallel. Rotation of the first tool member 2462 in the counter-clockwise direction illustrated by the arrow $AA_1$, causes the first tool member 2462 to intersect with the second tool member 2482 such that a gap exists in the lateral direction between the contact portion 2464 and the contact portion 2484. The gap G enables cutting force to be focused on a small cutting location or point (e.g., at the first cut point X1 or at the second cut point X2), rather than an extended cutting length or cutting area, and prevents clogging from the object to be cut.

Figure 8:
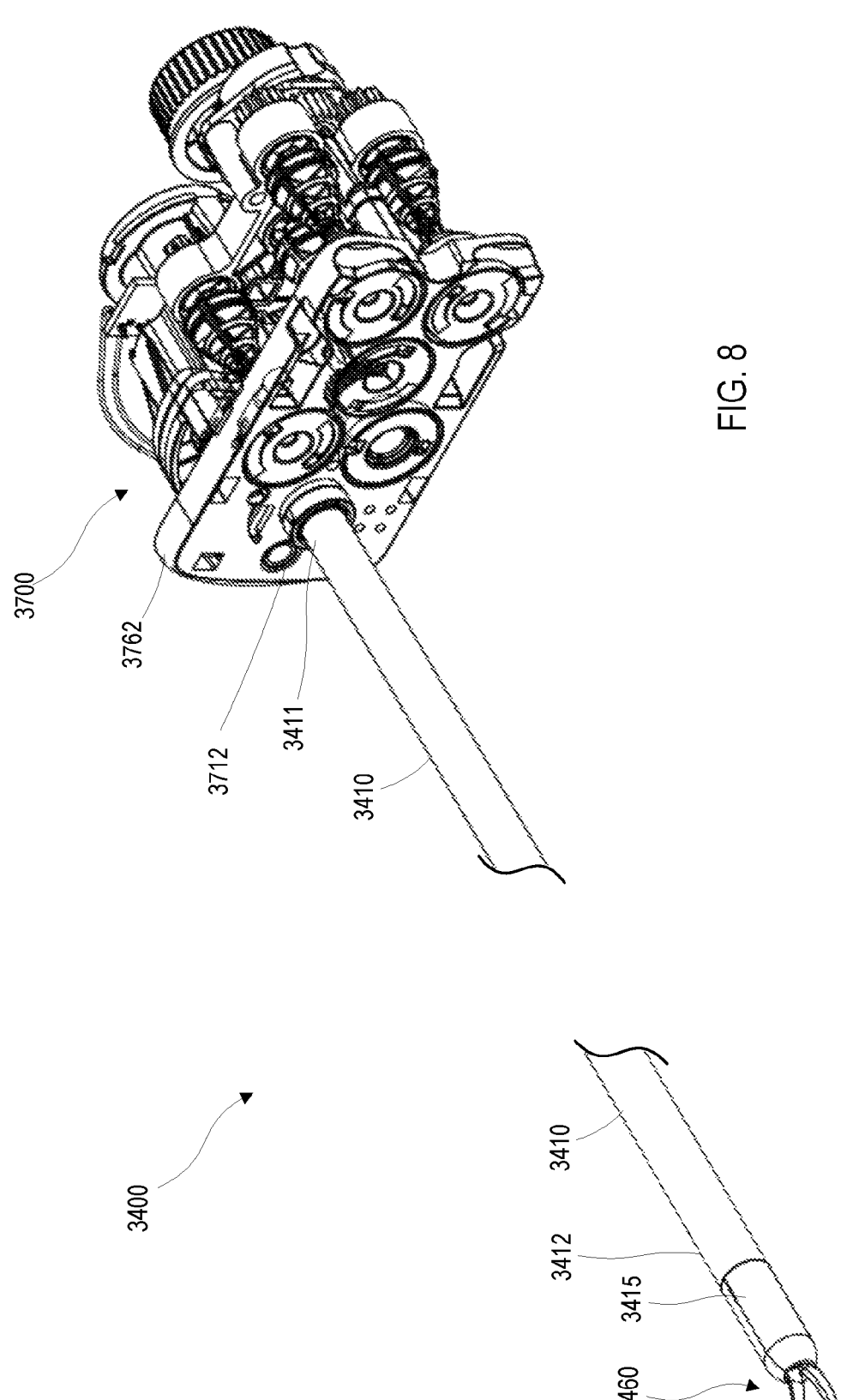
FIG. 8 is a perspective view of a medical device according to an embodiment.
Figure 9:
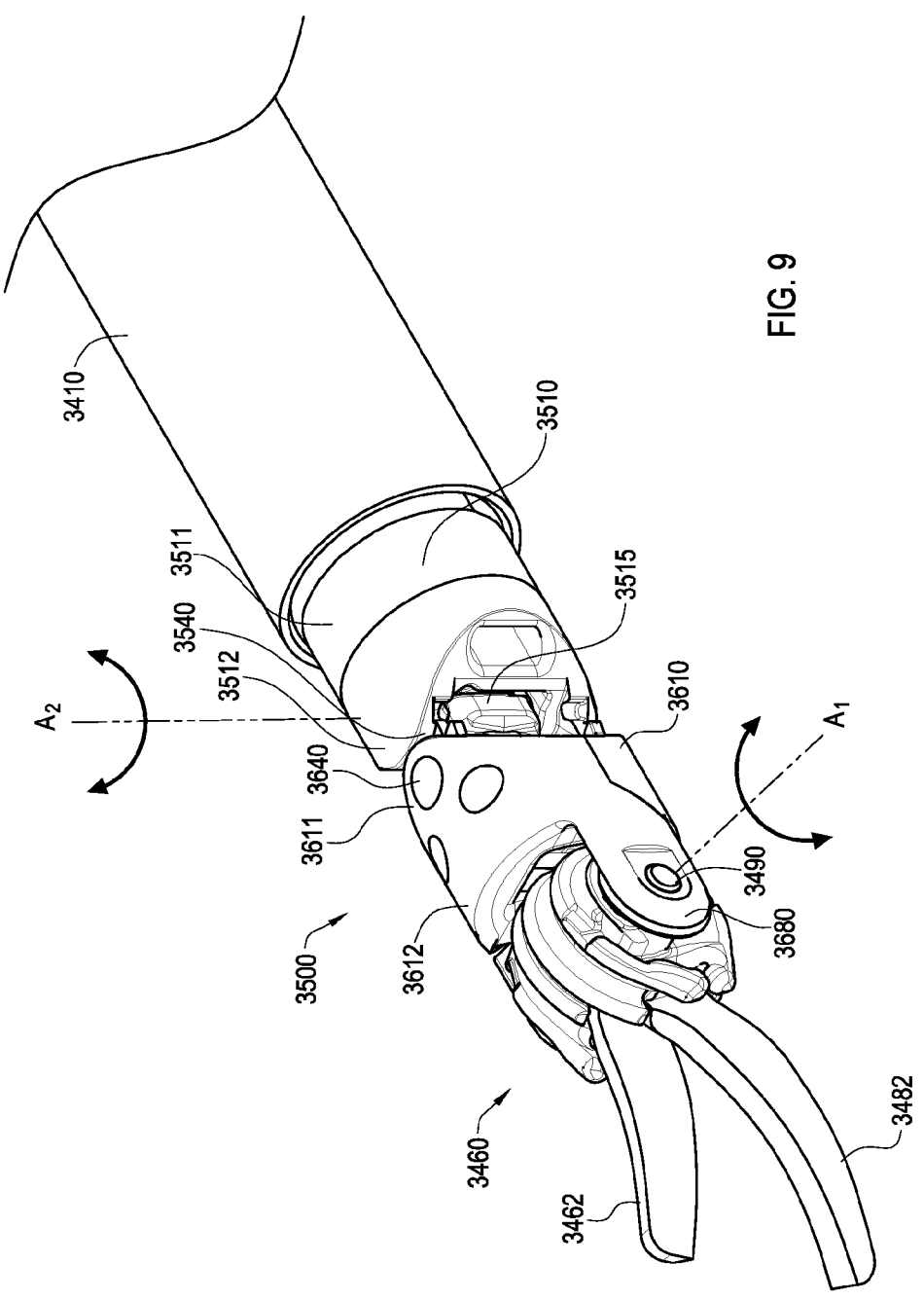
FIG. 9 is a perspective view of the distal end portion of the medical device of FIG. 8 with an outer cover removed and the end effector in an open configuration.
Figure 10:
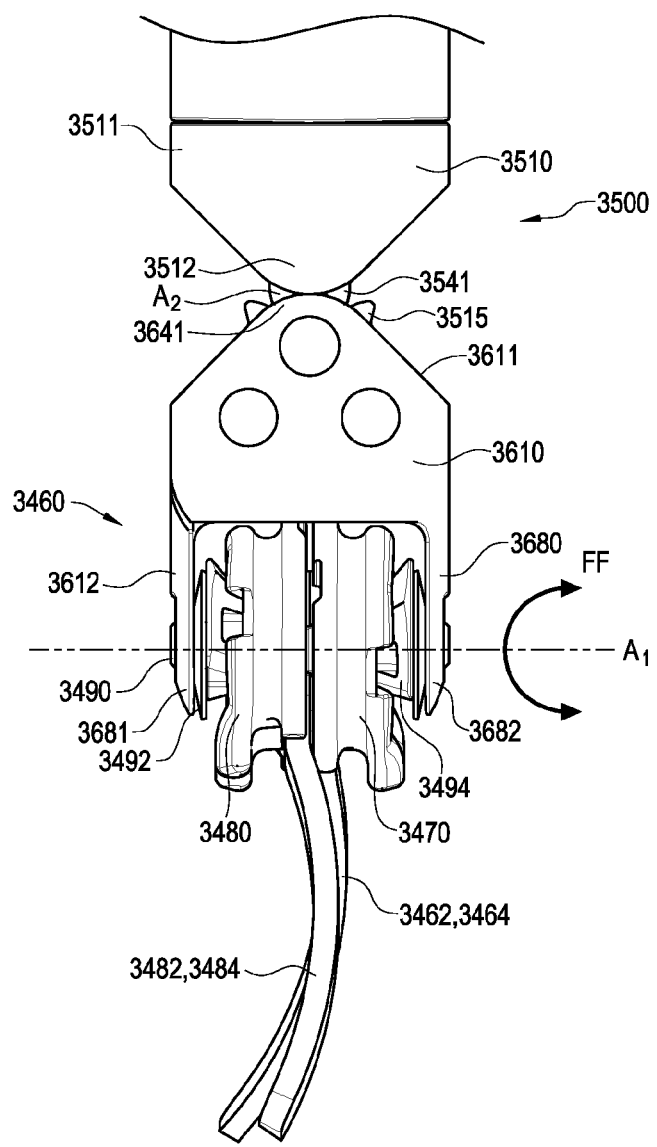
FIG. 10 is a top view of the distal end portion of the medical device of FIG. 8 with the outer cover removed and the end effector in the open configuration.

FIGS. 8-10 are various views of an instrument 3400, according to an embodiment. In some embodiments, the instrument 3400 or any of the components therein are optionally parts of a surgical system that performs surgical procedures, and which can include a manipulator unit, a series of kinematic linkages, a series of cannulas, or the like. The instrument 3400 (and any of the instruments described herein) can be used in any suitable surgical system, such as the MIRS system 1000 shown and described above. The instrument 3400 includes a proximal mechanical structure 3700, a shaft 3410, a distal wrist assembly 3500, a distal end effector 3460, and a distal cover 3415. Although not shown, the instrument 3400 also includes a first cable 3420 and a second cable 3430) (see e.g., FIG. 16A) that couple the proximal mechanical structure 3700 to the distal wrist assembly 3500 and end effector 3460. The instrument 3400 is configured such that movement of the first cable 3420 and second cable 3430 produces rotation of the end effector 3460 about a first axis of rotation $A_1$ (see FIGS. 9 and 10, which functions as a yaw axis, the term yaw is arbitrary), rotation of the wrist assembly 3500 about a second axis of rotation $A_2$ (see FIGS. 9 and 10, which functions as a pitch axis), a cutting rotation of the tool members of the end effector 3460 about the first axis of rotation $A_1$, or any combination of these movements. Changing the pitch or yaw of the instrument 3400 can be performed by manipulating the cables in a similar manner as that described above for the instrument 2400. Thus, the specific movement of each of the cables to accomplish the desired motion is not described below.

The shaft 3410 can be any suitable elongated shaft that couples the wrist assembly 3500 to the mechanical structure 3700. Specifically, the shaft 3410 includes a proximal end 3411 that is coupled to the mechanical structure 3700, and a distal end 3412 that is coupled to the wrist assembly 3500 (e.g., a proximal link of the wrist assembly 3500). The shaft 3410 one or more passageways, through which the cables and other components (e.g., charged electrical wires, ground wires, or the like) can be routed from the mechanical structure 3700 to the wrist assembly 3500. In the example shown, the optional cover 3415 (see FIG. 8) is positioned over the wrist assembly 3500 and at least a portion of the end effector 3460.

Referring to FIGS. 9 and 10, the wrist assembly 3500 (also referred to as a joint assembly) includes a first link 3510, a second link 3610 and a third link 3515. The first link 3510 has a proximal portion 3511 and a distal end portion 3512. The proximal end portion is coupled to the shaft 3410. The proximal portion 3511 can be coupled to the shaft 3410 via any suitable mechanism. For example, in some embodiments, the proximal portion 3511 can be matingly disposed within a portion of the shaft 3410 (e.g., via an interference fit). In some embodiments, the proximal portion 3511 can include one or more protrusions, recesses, openings, or connectors that couple the proximal portion 3511 to the shaft 3410. For example, in some embodiments, a pin extends through a hole in the proximal portion 3511 and a corresponding hole in the shaft 3410. In some embodiments, the proximal portion 3511 can be welded, glued, or fused to the shaft 3410.

The distal end portion 3512 includes a joint portion 3540 that is rotatably coupled to a mating joint portion 3640 of the second link 3610 as described in more detail below. The second link 3610 has a proximal portion 3611 and a distal end portion 3612. The proximal portion 3611 includes a joint portion 3640 that is rotatably coupled to the joint portion 3540 of the first link 3510 to form the wrist assembly 3500 having the second axis of rotation $A_2$ about which the second link 3610 rotates relative to the first link as shown in FIGS. 9 and 10. The wrist assembly 3500 can include any suitable coupling mechanisms. In this embodiment, the first link 3510 is coupled to the third link 3515 via a pinned joint and the second link 3610 is coupled to the third link 3515 via a pinned joint. In this manner, the third link 3515 maintains the coupling between the first link 3510 and the second link 3610 during rotation of the second link 3610 relative to the first link 3510.

Further, as described above, the distal end portion 3512 of the first link 3510 includes a joint portion 3540 that is rotatably coupled to a mating joint portion 3640 at the proximal portion 3611 of the second link 3610. Specifically, the joint portion 3540 includes a series of teeth (not shown) that are spaced apart by recesses (not shown), and the joint portion 3640 includes a series of teeth (not shown) that are spaced apart by recesses (not shown). The series of teeth and recesses can be similar to those shown and described in U.S. Patent Application Pub. No. US 2017/0120457 $A_1$ (filed Feb. 20, 2015), entitled "Mechanical Wrist Joints with Enhanced Range of Motion, and Related Devices and Methods," or to those shown and described in International Application No. PCT/US18/64721 (filed Dec. 10, 2018), entitled "Medical Tools Having Tension Bands," each of which is incorporated herein by reference in its entirety. The teeth of the first link 3510 engage the teeth of the second link 3610 during rotation of the second link 3610 relative to the first link 3510. In addition, the joint portion 3540 has a curved surface 3541 that engages a curved surface 3641 of the joint portion 3640 during rotation of the second link 3610 relative to the first link 3510. Because the wrist joint (i.e., the joint between the first link 3510 and the second link 3610) is not a pinned joint, the second axis $A_2$ will move relative to the first link 3510 during rotation of the second link 3610. In other words, the location of the second axis $A_2$ will move (for example, as viewed in a top view) with the rolling movement of the second link 3610 relative to the first link 3510.

As shown in FIGS. 9 and 10, the end effector 3460 is coupled to the second link 3610. More specifically, the distal end portion 3612 of the second link 3610 includes a connector 3680 with clevis ears 3681, 3682 that are coupled to the end effector 3460 such that the end effector 3460 (e.g., tool members of the end effector) rotates relative to the wrist assembly 3500 about the first axis of rotation $A_1$ (see, e.g., FIG. 10). The second axis of rotation $A_2$ is non-parallel to the first axis of rotation $A_1$. The first axis $A_1$ also functions as a cutting axis as tool members rotate in opposition to each other as described in more detail below. The connector 3680 can be any suitable connector to rotatably couple the end effector 3460 to the wrist assembly 3500. For example, in some embodiments, the first link 3510 can include a clevis and a pin, such as the pinned joints shown and described in U.S. Pat. No. 9,204,923 B2 (filed Jul. 16, 2008), entitled "Medical Device Electronically Energized Using Drive Cables," which is incorporated herein by reference in its entirety.

As shown in FIGS. 11A-11D, the end effector 3460) includes a first tool member 3462 (which functions as a first blade) and a second tool member 3482 (which functions as a second blade). The first tool member 3462 is a curved blade with a first contact portion 3464, and the second tool member 3482 is a curved blade with a second contact portion 3484. The first and second contact portions 3464, 3484 engage and contact opposite sides of an object to be cut. The first tool member 3462 is mounted to a first blade support 3860 and the second tool member 3482 is mounted to a second blade support 3880. In this example, the first blade support 3860 and the second blade support 3880 are identical components, which can reduce manufacturing and assembly costs by reducing the total number of unique parts and allowing the blade support to be used interchangeably on both sides the end effector 3460. Accordingly, the features described for the first blade support 3860 (e.g., the bore 3861 and discontinuity 3864) are included in and applicable to the second blade support 3880. In other embodiments, however, the first blade support 3860 and the second blade support 3880 can be different components. In some embodiments, one or more of the first and second blade supports 3860, 3880 are 17-4 stainless steel. In some embodiments, the first blade support and/or the second blade supports 3860, 3880 are each monolithically formed via metal injection molding.

The first blade support 3860 includes a bore 3861, an inner support portion 3866, and an outer support portion 3867. The inner support portion includes an inner wall portion 3866a and an outer wall portion 3866b. A recess defined between the inner wall portion 3866a and an outer wall portion 3866b is sized to receive and retain the first tool member 3462. The inner support portion further includes a hard stop protrusion 3871 and a hard stop groove 3872.

Figure 11A:
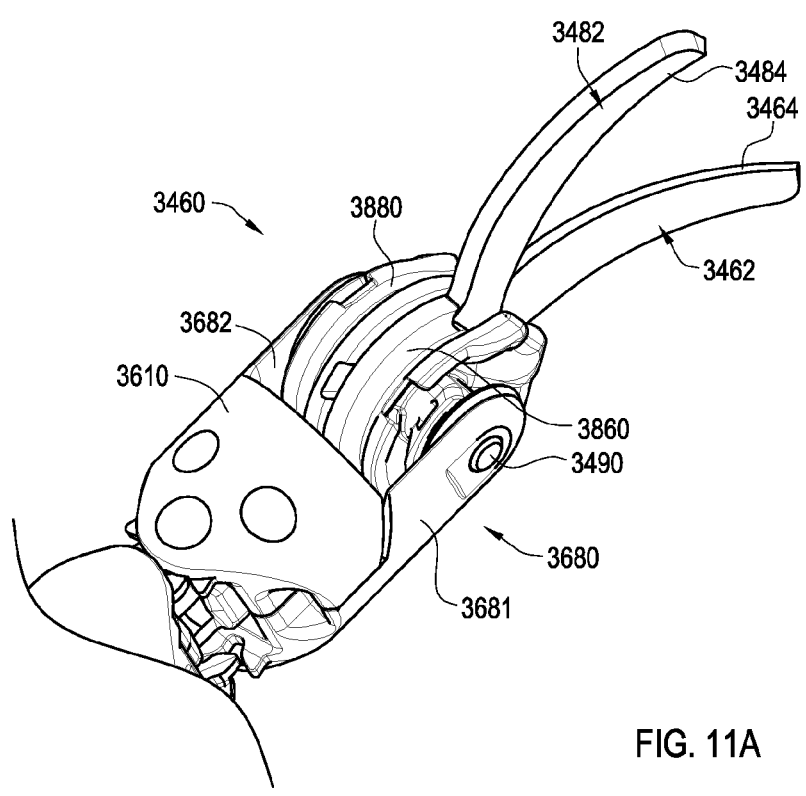
FIG. 11A is a perspective view of the end effector of the medical device of FIG. 8 with an outer cover removed and the end effector in the open configuration.
Figure 11B:
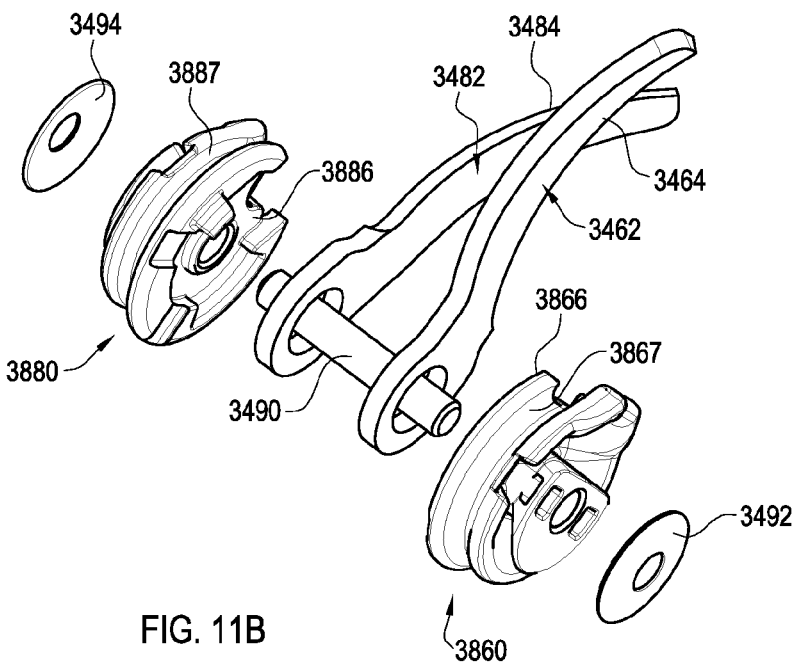
FIG. 11B is an exploded view of the end effector of FIG. 11A.
Figure 11D:
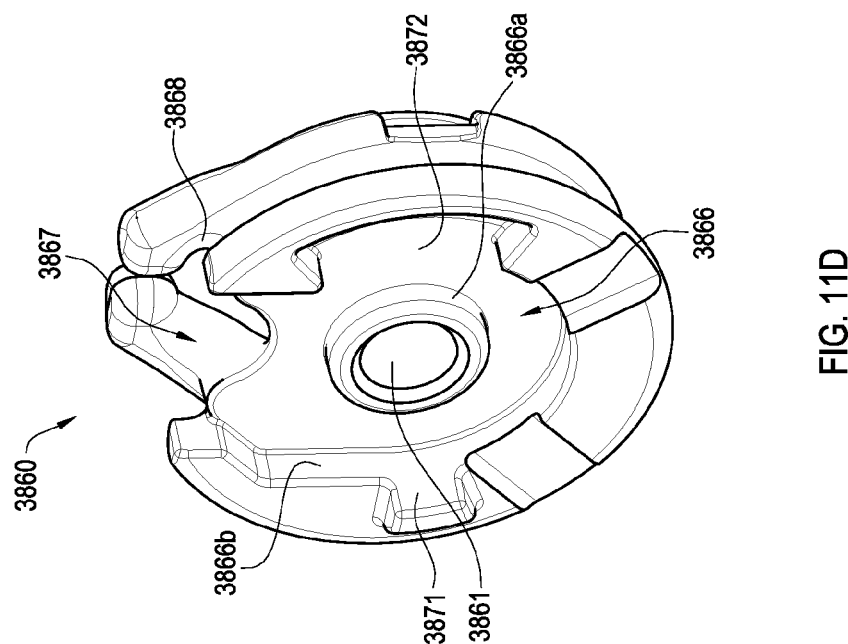
FIG. 11C is an enlarged view of the second blade support and FIG. 11D is an enlarged view of the first blade support of the end effector of FIG. 11A illustrating corresponding engagement features.
Figure 11C:
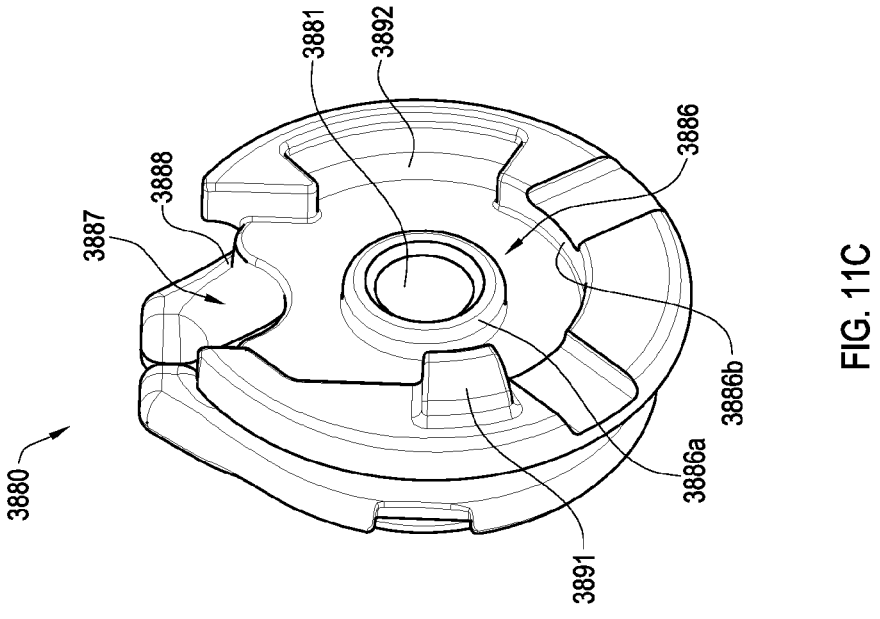

The second blade support 3880 includes a bore 3881, an inner support portion 3886, and an outer support portion 3887. The inner support portion 3886 includes an inner wall portion 3886a and an outer wall portion 3886b. A recess defined between the wall portion 3886a and an outer wall portion 3886b is sized to receive and retain the first tool member 3462. The inner support portion further includes a hard stop protrusion 3891 and a hard stop groove 3892. As generally shown in FIGS. 11B-11D, the two blade supports 3860, 3880 are assembled together on the pin 3490. Two spring members 3492, 3494 are sandwiched between the clevis ears 3681, 3682 to bias the first and second blade supports 3860, 3880 towards a center of the end effector 3460. Similarly stated, the spring member 3492 urges the first blade support 3860 away from the clevis ear 3681 and towards the second blade support 3880. The spring member 3494 urges the second blade support 3880 away from the clevis ear 3682 and towards the first blade support 3860. In some embodiments, the spring members 3492, 3494 are Belleville washers. In some embodiments, the Belleville washer are made of 17-7 stainless steel.

The hard stop protrusion 3871 (of the first blade support 3860) extends into the hard stop groove 3892 (of the second blade support 3880), and the hard stop protrusion 3891 (of the second blade support 3880) extends into the hard stop groove 3872 (of the first blade support 3860). The hard stop grooves 3872, 3892 limit the rotational travel of the first and second blade supports 3860, 3880) (and therefore the first and second tool members 3462, 3482) about a longitudinal axis of the pin 3490. Additionally, because the first and second blade supports 3860, 3880 are configured to tilt at their respective discontinuities 3864, 3884, the hard stop protrusion 3871, 3891 each include a height sufficient to interface with the hard stop grooves 3872, 3892, respectively, even when one or more of the first and second blade supports 3860, 3880 are tilted away from each other.

As shown in FIGS. 12A-12D, the outer support portions 3867, 3887 include a drive pulley 3868, 3888 and a coupling spool 3869, 3889. In this embodiment, the drive pulley 3868, 3888 and coupling spool 3869, 3889 can be formed as an integral or monolithic component that is welded (or otherwise coupled) to the inner support portion 3866, 3886, and the drive pulley 3868, 3888 and coupling spool 3869, 3889 can be formed as an integral or monolithic component. In some embodiments, the drive pulley 3868, 3888 and coupling spools 3869, 3889 can be configured the same as or similar to, and function the same as or similar to, the drive pulleys and coupling spools shown and described in International PCT Application No. PCT/US2021/017840 (filed Feb. 12, 2021), which is incorporated herein by reference in its entirety.

The end effector 3460 can be operatively coupled to the mechanical structure 3700) such that the tool members 3462 and 3482 rotate about the axis of rotation $A_1$. For example, the drive surface (which includes a groove) of the drive pulley 3868 is configured to engage the first cable 3420 such that a tension force exerted by the first cable 3420 along the drive surface produces a rotation torque about the rotation axis $A_1$. Similarly, the drive surface (which includes a groove) of the drive pulley 3888 is configured to engage the second cable such that a tension force exerted by the second cable along the drive surface produces a rotation torque about the rotation axis $A_1$. In this manner, the contact portion 3464 of the tool member 3462 and the contact portion 3484 of the tool member 3482 can be actuated to engage, manipulate, cut, or cauterize a target tissue during a surgical procedure.

Figure 12A:
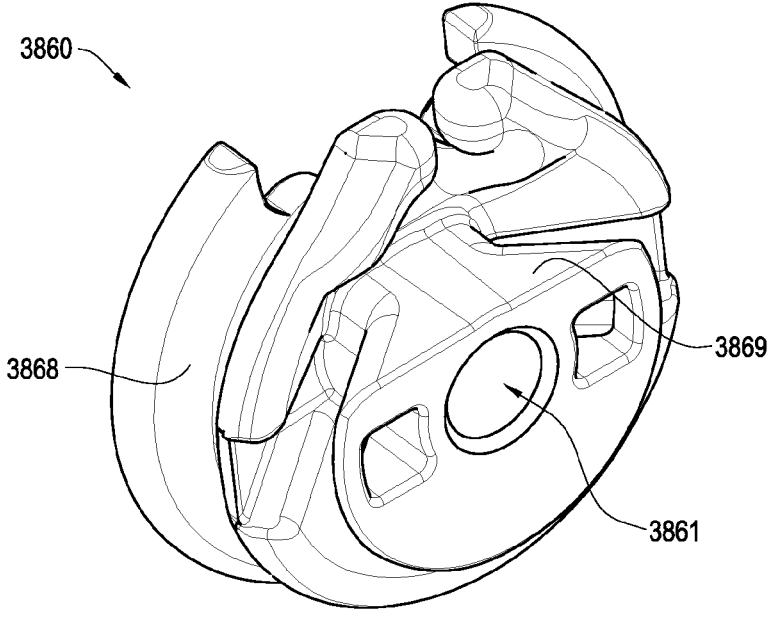
FIG. 12A is a front perspective view of a blade support of the end effector of FIG. 11A.
Figure 12B:
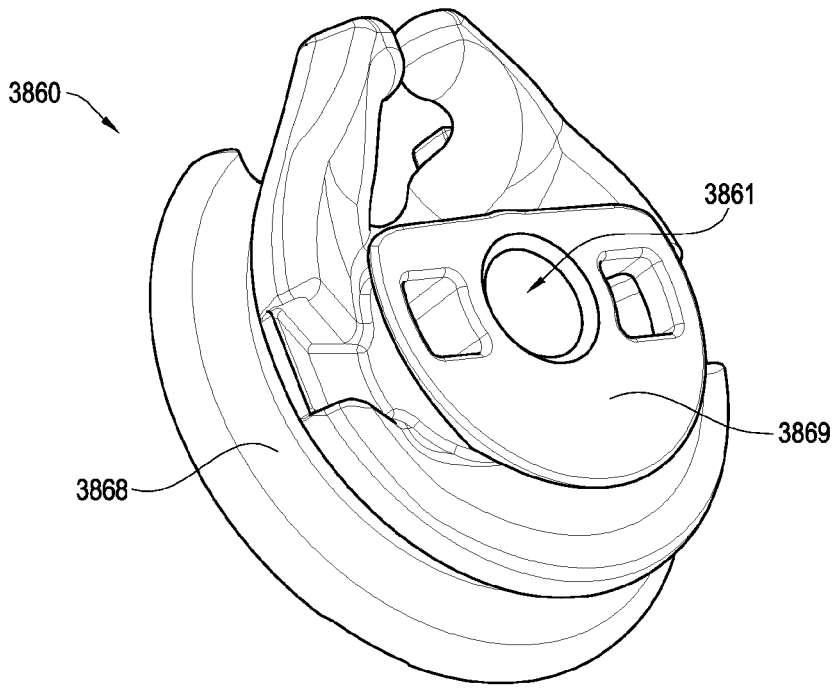
FIG. 12B is a side perspective view of a blade support of the end effector of FIG. 11A.
Figure 12C:
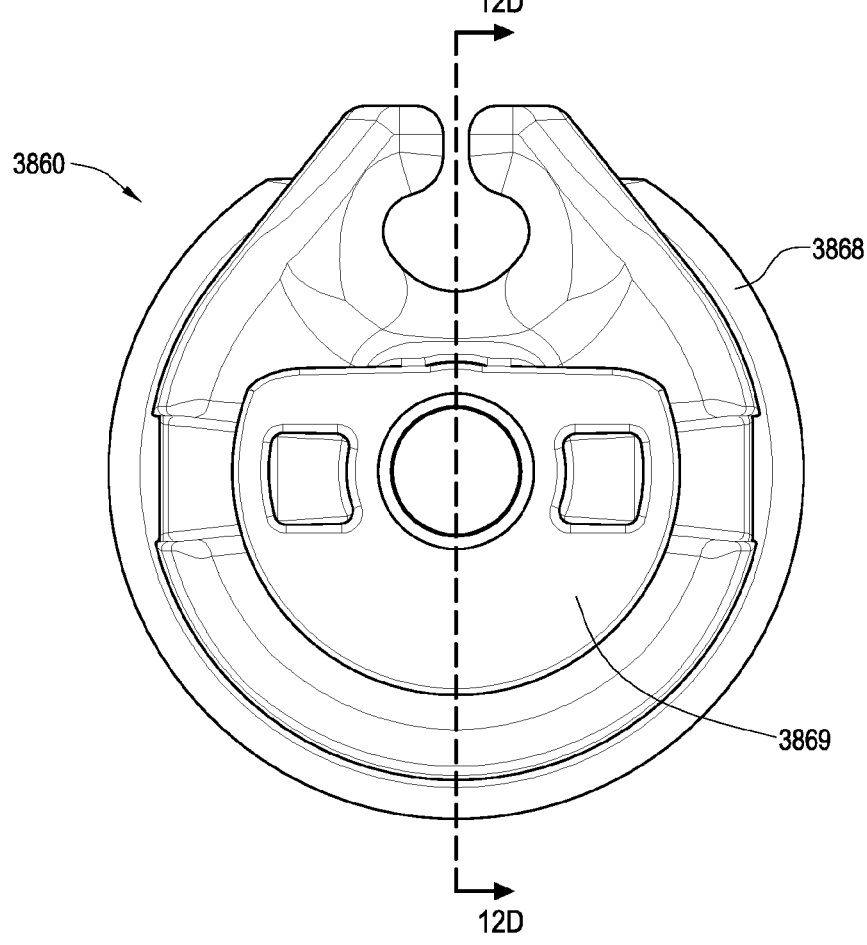
FIG. 12C is a front view of a blade support of the end effector of FIG. 11A.
Figure 12D:
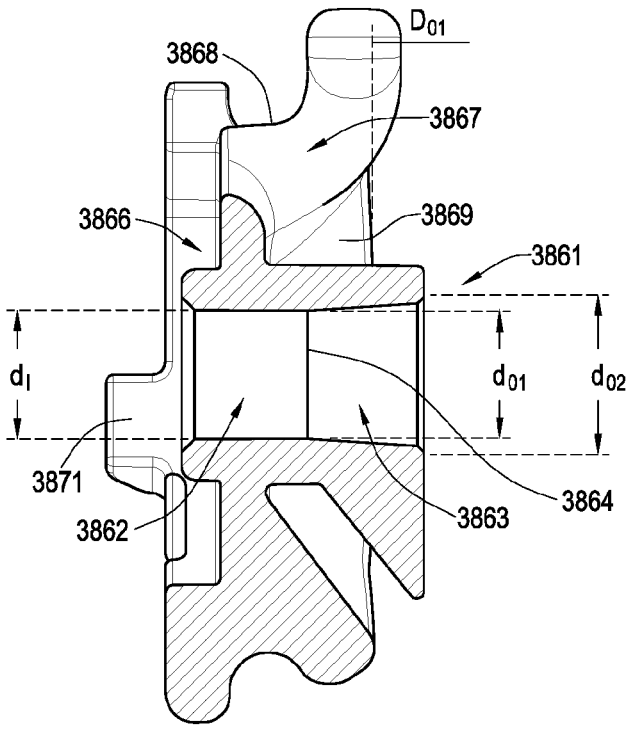
FIG. 12D is a cross-sectional view of the blade support of FIG. 12C taken at line 12-12.

FIG. 12D is a cross-sectional view of the first blade support 3860, which is the same as the internal structure of the second blade support 3880. Accordingly, certain features of the second blade support 3880 will be identified by the reference characters discussed below (e.g. the inner portion 3862 and the outer portion 3863). As shown in FIG. 12D, the blade support 3860 includes a bore 3861 having an inner portion 3862 and an outer portion 3863. The inner portion 3862 is oriented towards (or is closer to) the blade 3462 and the outer portion 3863 is oriented away from (or is further away from) the blade 3462. The bore 3861 has a discontinuity 3864 between the inner portion 3862 and the outer portion 3863 where the bore 3861 transitions from one cross-sectional area to another cross-sectional area along a length of the bore 3861. In this example, the inner portion 3862 of the bore 3861 can be provided with at least one cross-sectional area (shape and/or size) different from that of the outer portion 3863 of the bore 3861. The inner portion 3862 includes a cylindrical inner surface defined by a diameter $d_I$. The outer portion 3863 includes a truncated conical inner surface defined by a minor diameter $d_{O1}$ and a major diameter $d_{O2}$. The conical inner surface of the outer portion 3863 extends from a minor diameter $d_{O1}$ to a major diameter $d_{O2}$ in a direction away from the inner portion 3862. In some embodiments, the minor diameter $d_{O1}$ of the outer portion 3863 is greater than or equal to the diameter $d_I$ of the inner portion 3862. In this manner, the inner portion 3862 has a constant inner diameter and the outer portion 3863 is tapered, and the discontinuity 3864 is formed at the interface between the inner portion 3862 and the outer portion 3863. In other embodiments, however, the inner portion 2862 can be tapered (e.g., with a major diameter oriented towards (or is closer to) the blade 2462 and a minor oriented away from (or is further away from) the blade 2462, and/or the outer portion 2863 can have a constant inner diameter. By including the discontinuity 3864, the first blade support 3860 and therefore the blade 3462 can rotate (tilt) relative to the pin 3490) about the tilt axis $A_{T1}$ as described below (see FIGS. 13A-16B). Similarly, the second blade support 3880 and therefore the blade 3882 can rotate (tilt) relative to the pin 3490 about the tilt axis $A_{T2}$ in a direction opposite of the first blade support 3860.

The pin 3490) extends through the bore 3861 of the first blade support 3860 and through the bore 3861 of the second blade support 3880. The first tool member 3462 is coupled to the first blade support 3860 and is rotatable about the pin 3490 in a yaw degree of freedom. The second tool member 3482 is coupled to the second blade support 3880) and is rotatable about the pin 3490 in the yaw degree of freedom. In other words, the first and second blade supports 3860, 3880 are each independently rotatable about the yaw axis $A_1$ in a direction of arrows FF (see FIG. 10). As shown in FIGS. 13B and 14B, a yaw plane P is defined perpendicular to a longitudinal axis of the pin 3490) and along a center line of the end effector 3460.

Figure 13B:
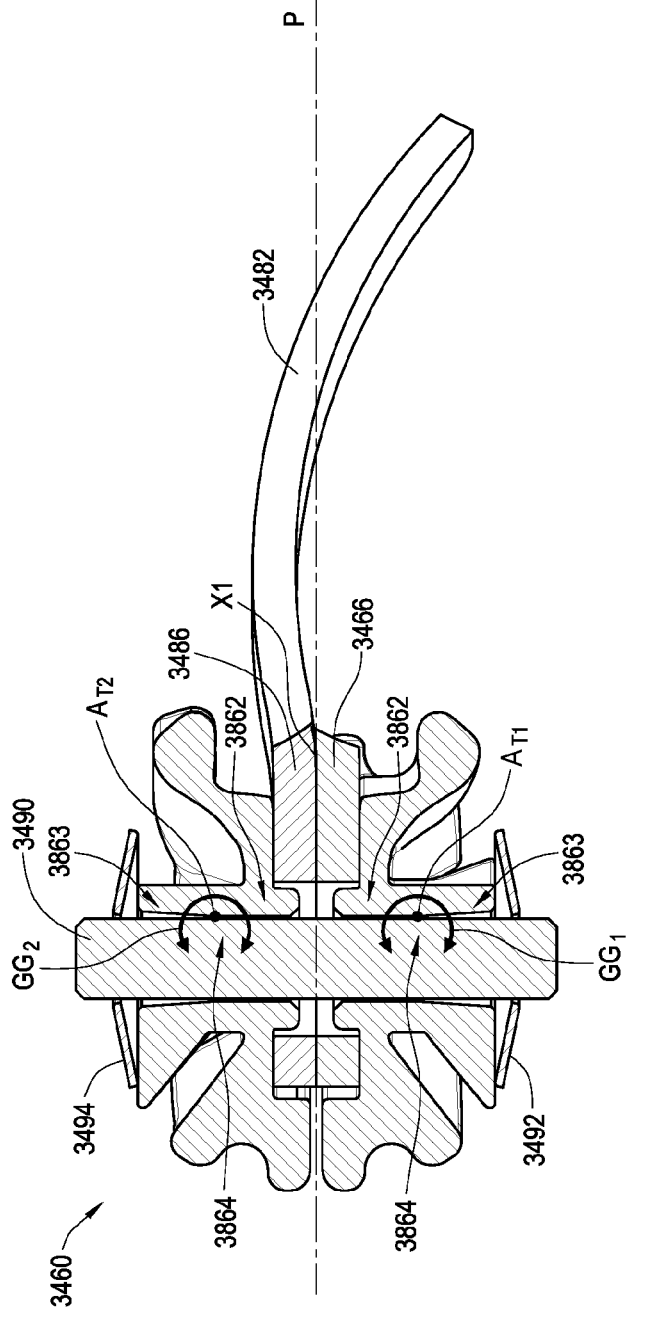
FIG. 13B is a cross-sectional view of the end effector of FIG. 13A taken at the line 13-13.
Figure 14A:
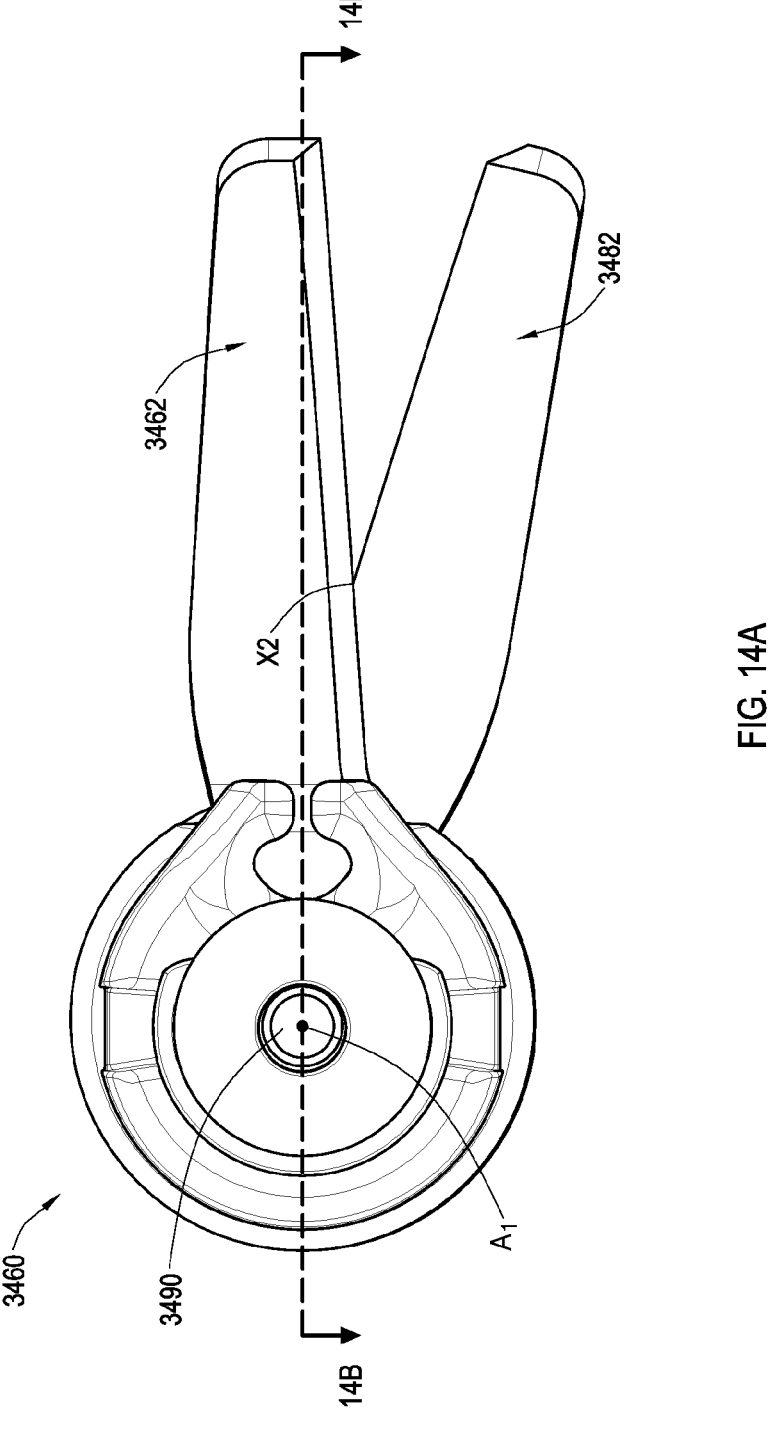
FIG. 14A is a side view of the end effector of the medical device of FIG. 13 in a second (partially closed) configuration.
Figure 14B:
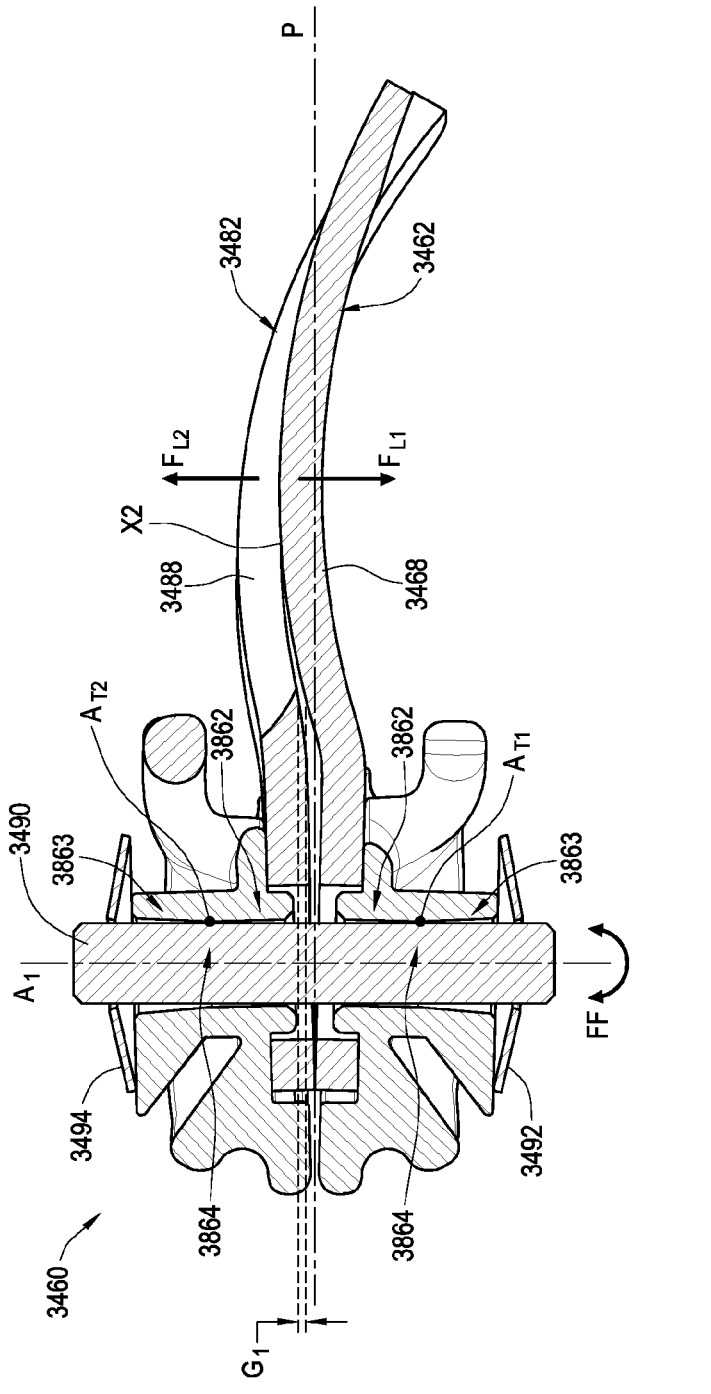
FIG. 14B is a cross-sectional view of the end effector of FIG. 14A taken at the line 14-14.
Figure 15A:
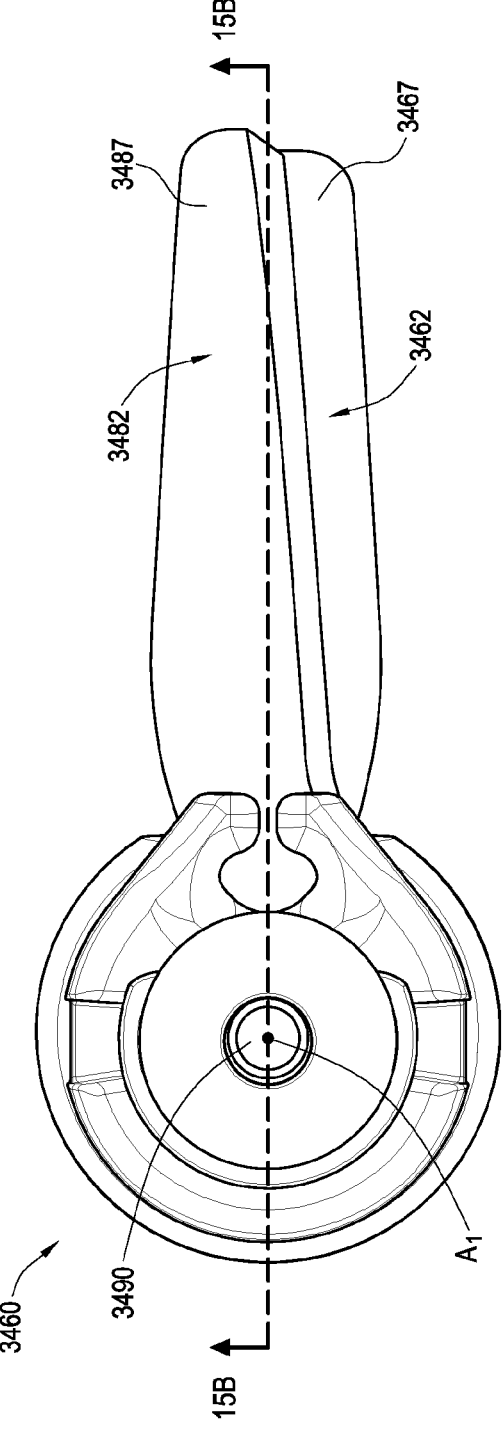
FIG. 15A is a side view of the end effector of the medical device of FIG. 13 in a third (fully closed) configuration.
Figure 15B:
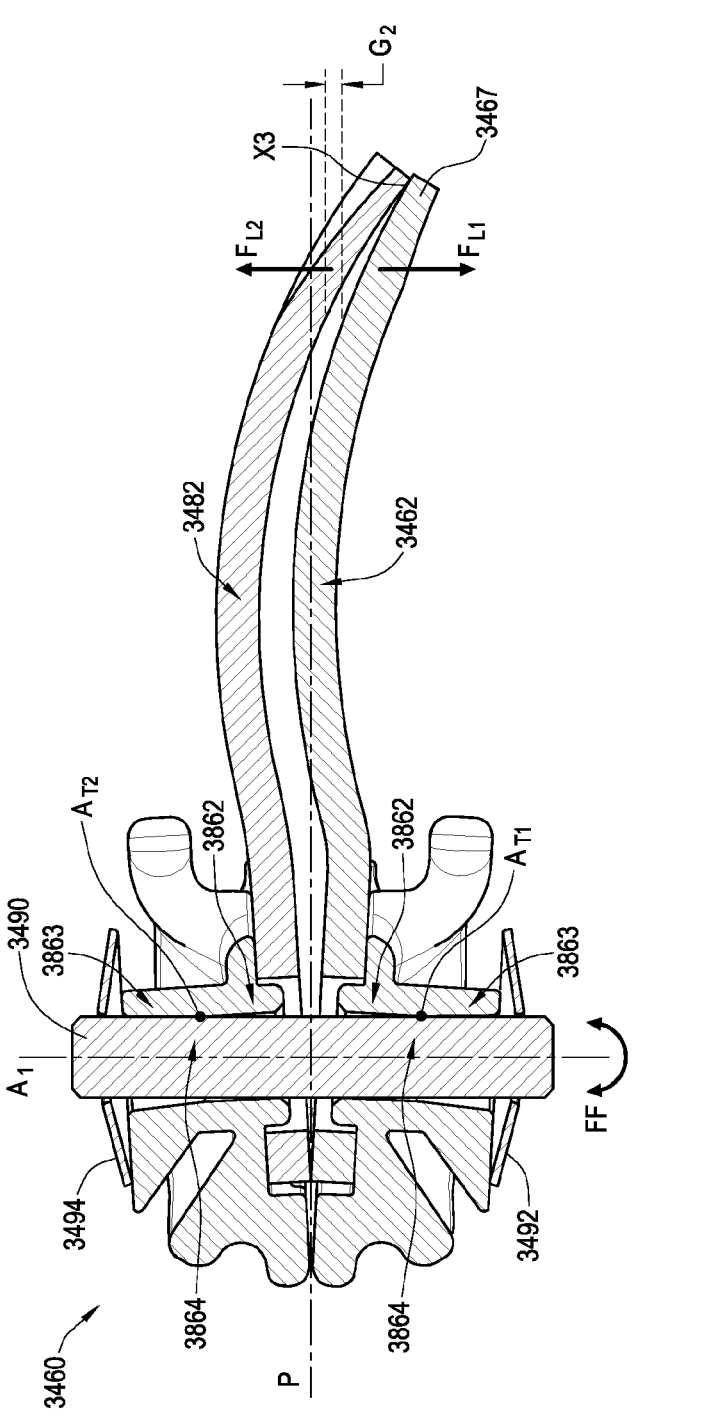
FIG. 15B is a cross-sectional view of the end effector of FIG. 15A taken at the line 15-15.

As shown in FIGS. 13B, 14B, and 15B, the first blade support 3860 is operable to tilt at the discontinuity 3864 of the bore 3861 in a first lateral direction away from the yaw plane P. The second blade support 3880 is operable to tilt at the discontinuity 3884 of its bore in a second lateral direction, opposite the first lateral direction, away from the yaw plane P. Stated in another manner, the first blade support 3860 tilts about a tilt axis $A_{T1}$ in a direction of arrows $GG_1$ relative to the pin 3490, and the second blade support 3880 tilts about a tilt axis $A_{T2}$ in a direction of arrows $GG_2$ relative to the pin 3490.

Figure 13A:
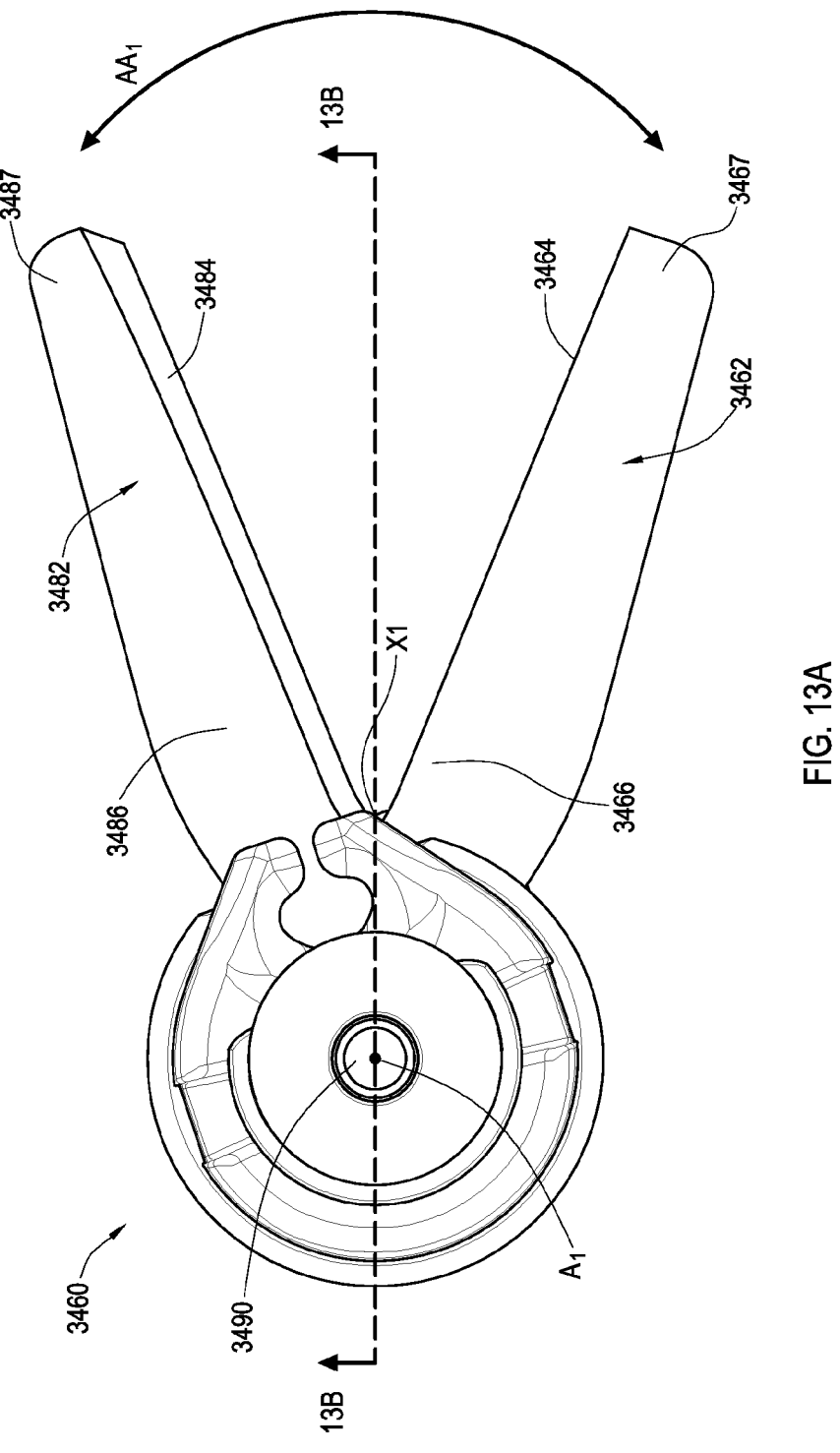
FIG. 13A is a side view of the end effector of the medical device of FIG. 8 in a first (open) configuration.

In a first configuration (open configuration) of the tool members 3462, 3482 as shown in FIGS. 13A and 13B, a proximal end portion 3466 of the first tool member 3462 and a proximal end portion 3486 of the second tool member 3482 contact and intersect to define a first cut point X1. In other words, the contact portion 3464 of the first tool member 3462 engages the contact portion 3484 of the second tool member 3482 at the first cut position X1 to cut a target tissue or object positioned between the first and second contact portions 3464, 3484. A distal end portion 3467 of the first tool member 3462 and a distal end portion 3487 of the second tool member 3482 overlap laterally to provide preload on the tool members 3462, 3482 as the tool members 3462, 3482 transitions from open to closed configurations. Stated in another manner, the distal end portion 3467 extends in a first lateral direction (e.g., extends to the left-hand side of the yaw plane P) away from the yaw plane P beyond the distal end portion 3487 extending in the first lateral direction away from the yaw plane P such that the distal end portion 3467 overlaps the distal end portion 3487. Additionally, or alternatively, the distal end portion 3487 extends in a second lateral direction (e.g., extends to the right-hand side of the yaw plane P) away from the yaw plane P beyond the distal end portion 3467 extending in the second lateral direction away from the yaw plane P such that the distal end portion 3487 overlaps the distal end portion 3467. In some embodiments, the overlap of the distal end portion 3467 and the distal end portion 3487 is a width of between about 1.27 mm (0.050 inches) to about 1.905 mm (0.075 inches). In some embodiments, the overlap of the distal end portion 3467 and the distal end portion 3487 is a width of between about 1.397 mm (0.055 inches) to about 1.651 mm (0.065 inches). In some embodiments, the overlap of the distal end portion 3467 and the distal end portion 3487 is a width of about 1.524 mm (0.060 inches).

As the tool members 3462, 3482 are rotated about the yaw axis $A_1$ from the first configuration (open) to a second configuration (partially closed) configuration, the cutting location translates along the contact portions 3464, 3484 to the second cut position X2 (see FIGS. 14A and 14B). In particular, as the tool members 3462, 3482 are rotated to close upon one another in the direction illustrated by the arrow $AA_1$ (clockwise direction for the first tool member 3462 and counter-clockwise direction for the second tool member 3482), a distal end portion 3467 of the first tool member 3462 begins to approach a distal end portion 3487 of the second tool member 3482. An intermediate portion 3468 of the first tool member 3462 contact and intersect an intermediate portion 3488 of the first tool member 3482 to define the second cut point X2. From the first cut point X1 to the second cut point X2, rotation of the tool members 3462, 3482 will cause opposing lateral forces $F_{L1}$, $F_{L2}$ to be applied on the tool members 3462, 3482. The interference between the first tool member 3462 and the second tool member 3482 causes a first lateral force $F_{L1}$ (downward direction in the figure) on the first tool member 3462, which in turn causes the first blade support 3860 to tilt about the tilt axis $A_{T1}$. Additionally, the interference between the first tool member 3462 and the second tool member 3482 causes a second lateral force $F_{L2}$ (upward direction in the figure) on the second tool member 3482, which in turn causes the second blade support 3880 to tilt about the tilt axis $A_{T2}$. Proximal to the second cut point X2, a gap $G_1$ separating the tool members 3462, 3482 is formed due to the curvature of the blades and the tilt of the first and second blade supports 3860, 3880. The gap $G_1$ enables cutting force to be focused on a small cutting location or point (e.g., at the second point X2), rather than an extended cutting length or cutting area, and prevents clogging from the object to be cut. For example, in some embodiments, a width of the gap $G_1$ is between about 0.203 mm (0.008 inches) to about 0.254 mm (0.010 inches).

As the tool members 3462, 3482 are further rotated about the yaw axis $A_1$ from the second configuration (partially closed) to a third configuration (closed) configuration, the cutting location translates along the contact portions 3464, 3484 to the third cut position X3 (see FIGS. 15A and 15B). In particular, the distal end portion 3467 of the first tool member 3462 contact and intersect the distal end portion 3487 of the second tool member 3482 to define the third cut point X3. From the second cut point X2 to the third cut point X3, rotation of the tool members 3462, 3482 will cause opposing lateral forces $F_{L3}$, $F_{L4}$ to be applied on the tool members 3462, 3482. The interference between the first tool member 3462 and the second tool member 3482 causes a first lateral force $F_{L3}$ (downward direction in the figure) on the first tool member 3462, which in turn causes the first blade support 3860 to further tilt about the tilt axis $A_{T1}$. Additionally, the interference between the first tool member

3462 and the second tool member 3482 causes a second lateral force $F_{L4}$ (upward direction in the figure) on the second tool member 3482, which in turn causes the second blade support 3880 to further tilt about the tilt axis $A_{T2}$. Proximal to the second cut point X2, a gap $G_2$ separating the tool members 3462, 3482 is formed due to the curvature of the blades and the tilt of the first and second blade supports 3860, 3880. The gap $G_2$ enables cutting force to be focused on a small cutting location or point (e.g., at the second point X3), rather than an extended cutting length or cutting area, and prevents clogging from the object to be cut. In some embodiments, a width of the gap $G_2$ is between about 0.457 mm (0.018 inches) to about 0.508 mm (0.020 inches).

As shown in FIGS. 11A, 11B, 14B and 15B, the first tool member 3462 and the second tool member 3482 include curved cutting blades. In addition to causing the first blade support 3860 and the second blade support 3880 to tilt at their respective discontinuities 3864, the opposing lateral forces $F_{L1}$, $F_{L2}$ cause the first and second tool members 3462, 3482 to temporarily flex and deform away from each other. The tilting of the first and second blade supports 3860, 3880 at their respective discontinuities 3864 enable thinner and/or more malleable materials to be used for the first and second tool members 3462, 3482 without permanently deforming the first and second tool members 3462, 3482 during operation (e.g., transitioning repeatedly back and forth from the first cut point X1 to the third cut point X3). In some embodiments, at the first cut point X1, the first and second tool members 3462, 3482 each flex about 0.0508 mm (0.002 inches). In some embodiments, the first blade support 3860 tilts between about 1 to 10 degrees at the discontinuity 3864 about the tilt axis $A_{T1}$. In some embodiments, the first blade support 3860 tilts between about 3 to 8 degrees at the discontinuity 3864 about the tilt axis $A_{T1}$. In some embodiments, the second blade support 3880 tilts between about 1 to 10 degrees at the discontinuity 3864 about the tilt axis $A_{T2}$. In some embodiments, the second blade support 3880 tilts between about 3 to 8 degrees at the discontinuity 3864 about the tilt axis $A_{T2}$.

In some embodiments, the curvature of the first tool member 3462 is about 12.319 mm (0.485 inches) and the curvature of the second tool member 3482 is about 10.541 mm (0.415 inches). The curvature of the first and second tool members 3462, 3482, the flex of the first and second tool members 3462, 3482 as it transitions from the first cut point X1 to the third cut point X3, and the tilting of the first and second blade supports 3860, 3880 enable the starting cut point to begin closer toward the pin 3490. In some embodiments, at the third cut point X3, the first and second tool members 3462, 3482 each flex between about 0.127 mm (0.005 inches) to about 0.635 mm (0.025 inches). In some embodiments, at the third cut point X3, the first and second tool members 3462, 3482 each flex between about 0.635 mm (0.010 inches) to about 0.508 mm (0.020 inches). As described above, in some embodiments, the overlap of the distal end portion 3467 and the distal end portion 3487 is a width of about 1.524 mm (0.060 inches) when the end effector 3460 is in the first (open) configuration. In this example, when the end effector 3460 is then placed in the third (closed) configuration, the combined flex of the first and second tool members 3462, 3482 will be less than about 1.524 cm (0.60 inches) in part due to the tilting of the first and second blade supports 3860, 3880 and the lateral displacement of the first and second tool members 3462, 3482 occurring due to the tilting.

In some embodiments, the starting cut point is about 3.683 mm (0.145 inches) from the pin 3490. By enabling the starting cut point to be shifted proximally closer to the pin 3490, an overall length of the first and second tool members 3462, 3482 can be reduced, thereby improving maneuverability of the end effector 3460 within the work site.

Figure 16A:
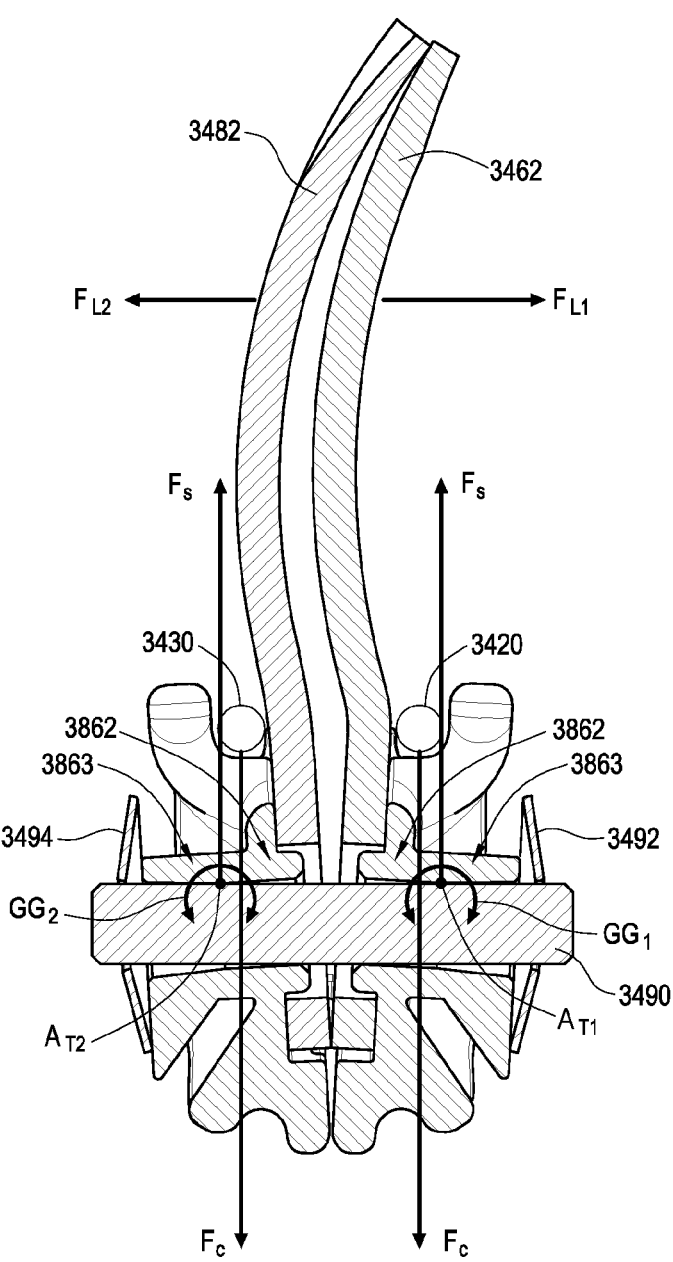
FIG. 16A is a cross-sectional view of the end effector of FIG. 15A taken at the line 15-15 showing the forces applied when an actuation member is mounted to the end effector
Figure 16B:
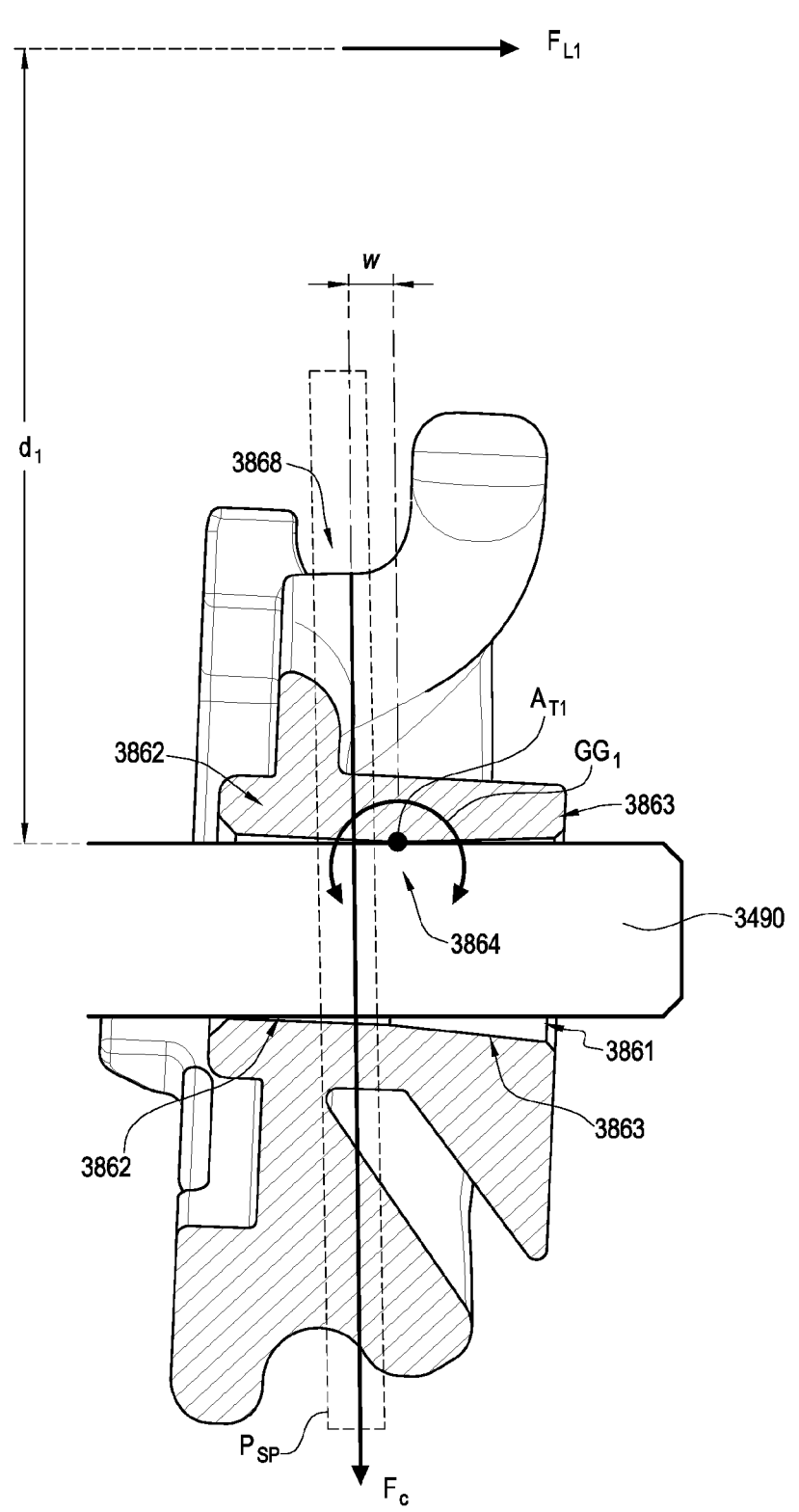
FIG. 16B is an enlarged cross-sectional view of a portion of the end effector shown in FIG. 16A.

FIGS. 16A and 16B illustrate the forces acting on the first and second tool member 3462, 3482 and the first and second blade supports 3860, 3880 when the end effector 3460 is in the third (fully closed) configuration. As described above, the interference between the first tool member 3462 and the second tool member 3482 causes a first lateral force $F_{L3}$ to be applied on the first tool member 3462 and a second lateral force $F_{L4}$ to be applied on the second tool member 3482. These lateral forces $F_{L3}$, $F_{L4}$ in turn causes the first blade support 3860 to rotate clockwise at the discontinuity 3864 (of the first blade support 3860) about the first tilt axis $A_{T1}$, and the second blade support 3880 to rotate counter-clockwise at the discontinuity 3864 (of the second blade support 3880) about the second tilt axis $A_{T2}$. Because the first and the second blade support 3860, 3880 are identical, FIG. 16B illustrates the forces and moments acting on the first blade support 3860. It will be apparent to one skilled in the art that forces and moments will act similarly on the second blade support 3880 in an opposite (mirrored) direction. As described herein, the first and second tool members 3462, 3482 are configured to close upon each other to cut an object. As the first and second tool members 3462, 3482 close upon each other, the cut point can transition from the first cut position X1 to the second cut position X2 to the third cut position X3, and any intermediate positions therebetween. As the first and second tool members 3462, 3482 are moved from an open configuration to a closed configuration, a perpendicular distance $d_1$ from the discontinuity 3864 to the first lateral force $F_{L3}$ increases (i.e., as the location of the lateral force moves distally away from the pin 3490). The first lateral force $F_{L3}$ together with the perpendicular distance $d_1$ generates a moment in a clockwise direction shown by the arrow $GG_1$. This causes the first blade support 3860 to tilt at the discontinuity 3864 in a clockwise direction about the tilt axis $A_{T1}$.

Additionally, a cable tension force $F_C$ is applied on the drive pulley 3868 in a direction towards the pin 3490. A solid plane $P_{SP}$ defined by the cable groove of the drive pulley 3868 intersects the inner portion 3862 of the bore 3861 such that tension of an actuating cable applied on the drive pulley 3868 does not cause the first blade support 3860 to tilt at the discontinuity 3864 in a counter-clockwise direction shown by the arrow $GG_1$. In other words, a perpendicular distance w from the discontinuity 3864 to the cable tension force $F_C$ is selected such that a moment generated by the cable tension force $F_C$ does not contribute towards excessive deformation of the first and second tool member 3462, 3482. By preventing excessive deformation, plastic deformation of one of the first and second tool member 3462, 3482 is prevented. The location where the cable tension force $F_C$ is applied relative to the tilt axis $A_{T1}$ also separates influence of the cable load on the first and second tool member 3462, 3482. Minimizing the influence of the cable tension force $F_C$ on the first and second tool member 3462, 3482 also enables a gap to be maintained during a cutting procedure and prevents the first contact portion 3464 and the second contact portion 3484 from tracking one another (e.g., being stacked on top or parallel with one another). If the first and second contact portions 3464, 3484 track one another, rather than crossing over such that a gap is formed between the first and second tool member 3462, 3482, the cutting point becomes a longer cutting length and reduces cutting effectiveness. In this manner, the tilt provided by the first and second blade supports 3860, 3880 allow the first and second tool members 3462, 3482 to move laterally away from the yaw plane P a greater amount than through deformation of the first and second tool members 3462, 3482 alone. This in turn enables the first and second tool members 3462, 3482 to be made thinner and/or using more malleable materials to reduce manufacturing and material costs. In some embodiments, the first and second tool members 3462, 3482 are stamped blades made of stainless steel. In some embodiments, the first and second tool members 3462, 3482 are made of 301 stainless steel. In some embodiments, a thickness of the first and second tool members 3462, 3482 is between about 0.508 mm (0.020) inches) to about 0.889 (0.035 inches). In some embodiments, a thickness of the first and second tool members 3462, 3482 is about 0.635 mm (0.025 inches) when a length of the blade is less than about 9.271 mm (0.365 inches). In some embodiments, a thickness of the first and second tool members 3462, 3482 is about 0.762 mm (0.030 inches) when a length of the blade is greater than or equal to about 9.271 mm (0.365 inches).

Figure 17B:
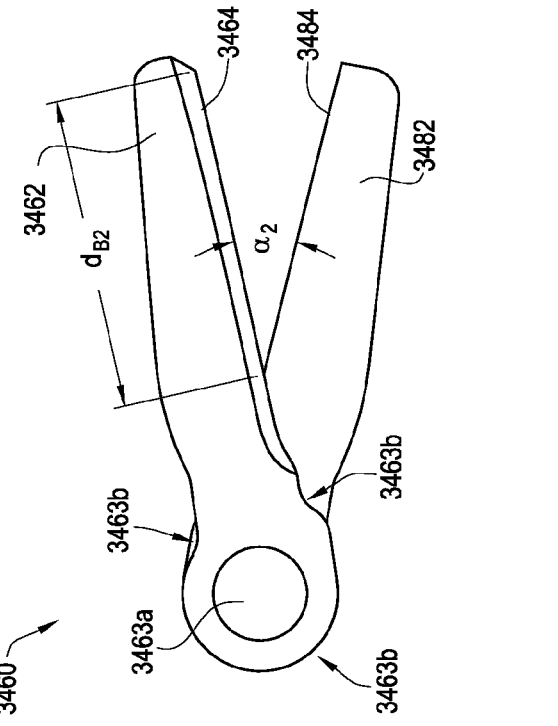
FIG. 17B is a side view of the first blade and the second blade of FIG. 17A in a second orientation.
Figure 17A:
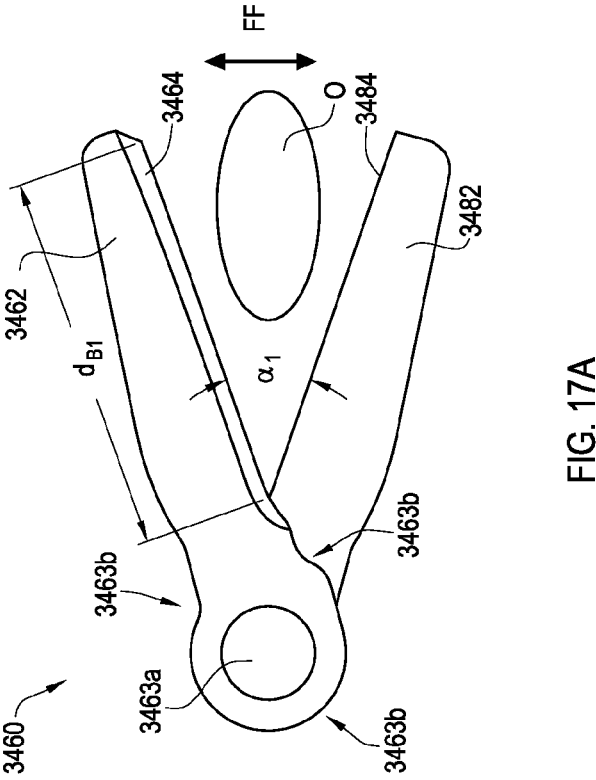
FIG. 17A is a side view a first blade and a second blade according to an embodiment in a first orientation.

FIGS. 17A and 17B show the first and second tool members 3462, 3482 according to an embodiment. The first tool member 3462 includes a mounting hole 3463a and a mounting rim 3463b. The mounting rim 3463b includes linear and non-linear sections. The mounting hole 3463a is configured to be seated on the inner wall portion 3886a of the inner support 3886 (see FIG. 11C). The mounting rim 3463b is configured to engage the outer wall portion 3886b of the inner support 3886. In this manner, the first tool member 3462 can be inserted into the inner support 3886. The shape of the mounting rim 3463b allows the first tool member 3462 to be inserted into the outer wall portion 3886b in a predetermined rotational orientation. In this manner, the first tool member 3462 can be placed in the correct rotational orientation relative to the first blade support 3860) during assembly. Although not shown, the second tool member 3482 includes a mounting hole and a mounting rim similar to that of the first tool member 3462.

As shown in FIG. 17A, the end effector 3460 is in a first open configuration. An exposed length $d_{B1}$ of the first contact portion 3464 is about 9.144 mm (0.36 inches) and the angle $\alpha_1$ defined between the first contact portion 3464 and the second contact portion 3484 is about 39.7 degrees. As shown in FIG. 17B, the end effector 3460 is in a second open configuration. An exposed length $d_{B2}$ of the first contact portion 3464 is about 7.595 mm (0.299 inches) and the angle $\alpha_2$ defined between the first contact portion 3464 and the second contact portion 3484 is about 26.7 degrees.

Figure 18:
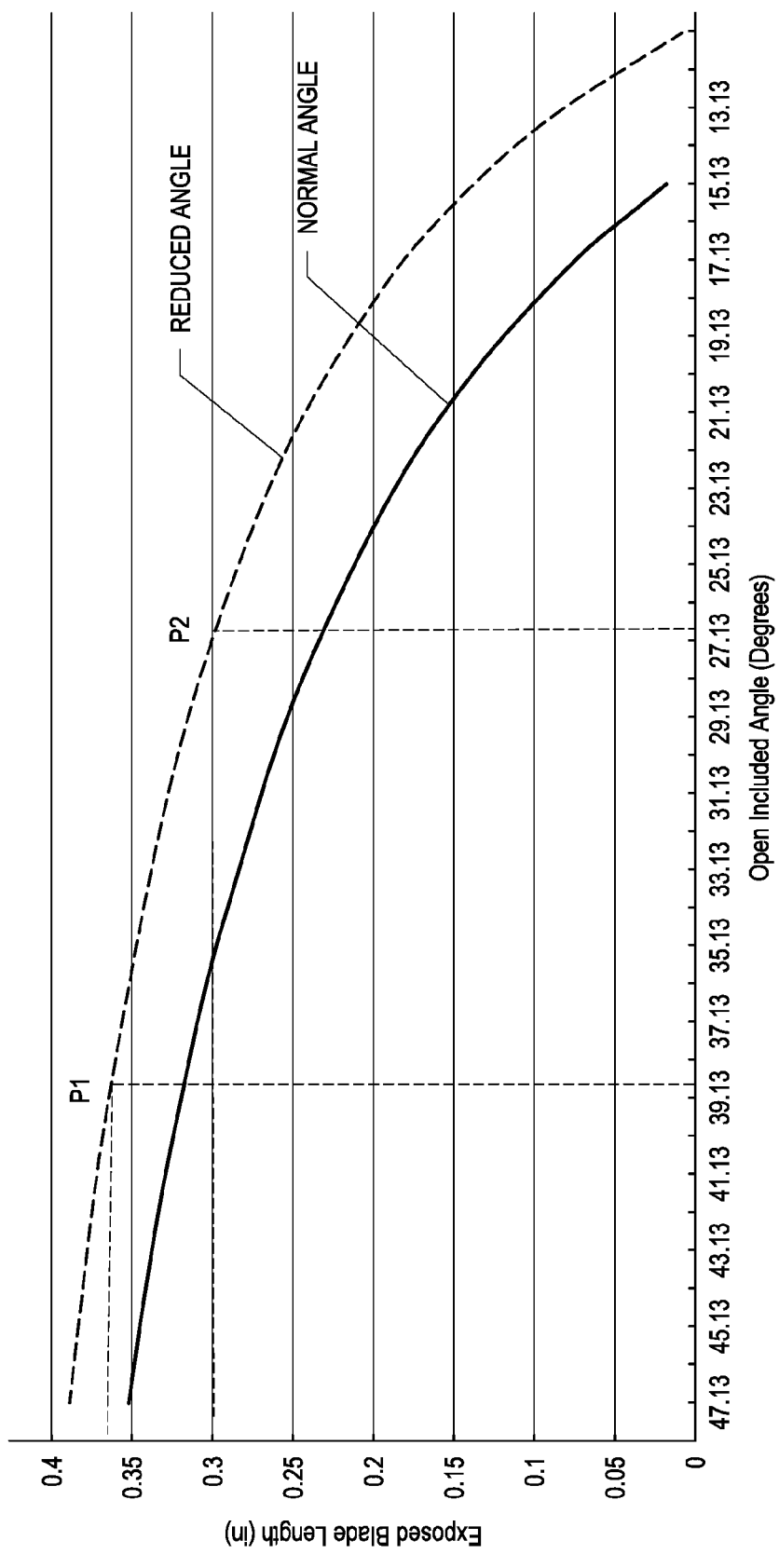
FIG. 18 is a chart showing an exposed blade length based on an open angle between the first blade and the second blade of FIGS. 17A and 17B transitioning between the first orientation and the second orientation.

By reducing the angle defined between the contact portions 3464, 3484 and providing a longer exposed blade length, distal pushing of material to be cut located between the contact portions 3464, 3484 is reduced. The reduced angle defined between the contact portions 3464, 3484 allows the first and second tool members 3462, 3482 to direct more cutting force in a direction, shown by the arrow FF, which is perpendicular to a proximal-to-distal direction of a material M, placed between the contact portions 3464, 3484 to be cut (see FIG. 17A). Thus, force transmitted through the contact portions 3464, 3484 contributes towards cutting or tearing of the material M rather than pushing the material M along the contact portions 3464, 3484. FIG. 18 is a plot depicting the exposed length of the first contact portion 3464 associated with an angle defined between the first and second contact portion 3464, 3484. In particular, the plot shows the exposed length $d_{B1}$ at the first open configuration P1 and the exposed length $d_{B2}$ at the second open configuration P2.

Figure 19:
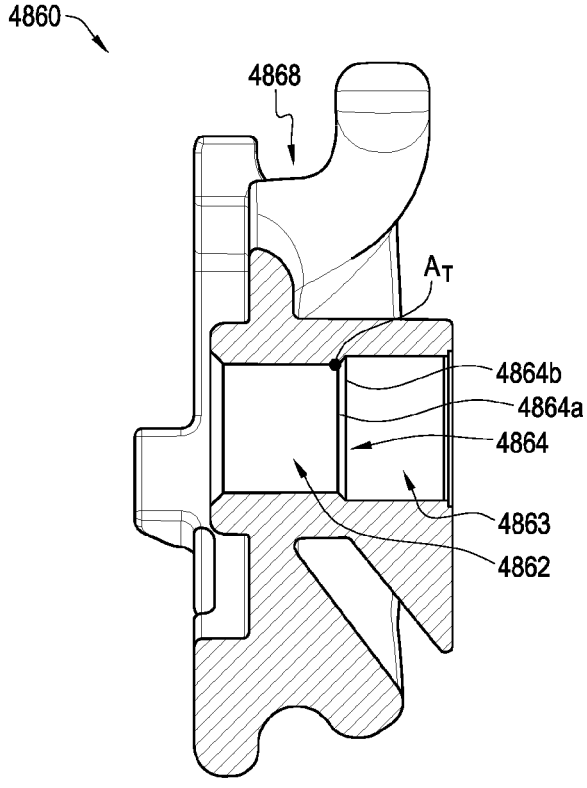
FIG. 19 is a cross-sectional view of a blade support according to an embodiment.

Although the first blade support 3860 described with reference to FIGS. 12D, 16A, and 16B includes a discontinuity 3864 at an interface between the inner portion 3862 with a constant inner diameter and the outer portion 3863 with a tapered inner surface and the discontinuity 3864, FIG. 19 depicts a blade support 4860 including an inner portion 4862 with a first constant inner diameter and an outer portion 4863 with a second constant inner diameter. The second constant inner diameter is greater than the first constant inner diameter. The discontinuity 4864 is formed at an interface between the inner portion 4862 and the outer portion 4863. In this example, the discontinuity 4864 includes a first inner diameter portion 4864*a* and a second inner diameter portion 4864*b*, the second inner diameter portion 4864*b* being greater than the first inner diameter portion 4864*a*. A tapered or beveled inner surface extends between the first inner diameter portion 4864*a* and the second inner diameter portion 4864*b*. As shown in FIG. 19, the first inner diameter portion 4864*a* is the same diameter as the inner diameter of the inner portion 4862. The second inner diameter portion 4864*b* is the same diameter as the inner diameter of the outer portion 4863. In some embodiments, the inner diameter of the outer portion 4863 is greater than the diameter of the second inner diameter portion 4864*b*. In some embodiments, the inner diameter of the inner portion 4862 is less than the diameter of the first inner diameter portion 4864*a*. The blade support 4860 functions in a similar manner as the blade supports described herein. In particular, when the blade support 4860 is rotatably supported on a pin and a tool member is mounted to the blade support 4860, force that is applied in a lateral direction on the tool member causes the blade support 4860 to rotate (tilt) relative to the pin about a tilt axis $A_T$ located at the discontinuity 4864. In some embodiments, a corner or edge of the first inner diameter portion 4864*a* serves as fulcrum about which the blade support 4860 can tilt on an outer circumferential surface of the pin.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a manipulator unit, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys or the like. Further, any of the links, tool members, tension members, or components described herein can be constructed from multiple pieces that are later joined together. For example, in some embodiments, a link can be constructed by joining together separately constructed components. In other embodiments however, any of the links, tool members, tension members, or components described herein can be monolithically constructed.

Although the instruments are generally shown as having an axis of rotation of the tool members (e.g., axis $A_1$) that is normal to an axis of rotation of the wrist member (e.g., axis $A_2$), in other embodiments any of the instruments described herein can include a tool member axis of rotation that is offset from the axis of rotation of the wrist assembly by any suitable angle.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. A medical device comprising:
a blade support, a blade supported by the blade support, and a pin;
wherein the blade support comprises a bore;
wherein the bore comprises an inner portion oriented toward the blade, an outer portion oriented away from the blade, and a discontinuity at a boundary between the inner portion and the outer portion of the bore;
wherein the pin extends through the bore of the blade support;
wherein the pin includes a first end and a second end opposite the first end;
wherein a longitudinal axis of the pin is defined between the first and second ends of the pin, a yaw plane is defined perpendicular to the longitudinal axis of the pin, a lateral direction is defined as a direction away from the yaw plane, and a rotational yaw degree of freedom is defined about the longitudinal axis of the pin; and
wherein the blade support rotates about the pin in the rotational yaw degree of freedom, contacts the pin at the discontinuity of the bore, and tilts away from the yaw plane at the discontinuity of the bore in response to a force applied in the lateral direction.

2. The medical device of claim 1, wherein:
the blade is a first blade;
in an unflexed state of the first blade in the lateral direction, the first blade has a first lateral curvature;
in a first flexed state of the first blade in the lateral direction, the first blade has a second lateral curvature straighter than the first lateral curvature;
in a second flexed state of the first blade in the lateral direction, the first blade has a third lateral curvature straighter than the second lateral curvature;
at a first cut point position on the first blade in relation to a second blade, the first blade is in the first flexed state or the second flexed state;
at a second cut point position on the first blade in relation to the second blade, the first blade is in a third flexed state; and the blade support tilts away from the yaw plane at the discontinuity of the bore as the first blade rotates from the first cut point position to the second cut point position.

3. The medical device of claim 1, wherein:

the blade support comprises an inner support portion oriented toward the blade and an outer support portion oriented away from the blade;

the inner support portion of the blade support supports the blade;

the outer support portion of the blade support comprises an actuating cable groove; and the actuating cable groove is positioned with reference to the discontinuity in the bore such that a tension in an actuating cable extending from the actuating cable groove away from the outer support portion of the blade support does not cause the blade support to tilt away from the yaw plane at the discontinuity of the bore.

4. The medical device of claim 1, wherein:

the medical device further comprises a cable;

the blade support comprises an inner support portion oriented toward the blade and an outer support portion oriented away from the blade;

the inner support portion of the blade support supports the blade;

the outer support portion of the blade support comprises a cable groove;

the cable is positioned in and extends away from the cable groove;

a tension on the cable away from the blade support urges the blade support to rotate about the pin in the rotational yaw degree of freedom; and the cable groove is positioned such that the tension on the cable does not cause the blade support to tilt away from the yaw plane at the discontinuity of the bore.

5. The medical device of claim 1, wherein:

contact between the outer portion of the bore and the pin limits tilting of the blade support at the discontinuity of the bore.

6. The medical device of claim 1, wherein:

the blade is a first blade and comprises a distal end portion;

the medical device further comprises a second blade;

the second blade rotates about the pin and comprises a distal end portion; and at a first yaw orientation in the rotational yaw degree of freedom of the first blade with reference to the second blade, the first blade contacts the second blade at a first cut point proximal of the distal end portion of the first blade, and the distal end portion of the first blade overlaps the distal end portion of the second blade in the yaw plane.

7. The medical device of claim 6, wherein:

at the first yaw orientation of the first blade with reference to the second blade, the first blade and the second blade are separated in the lateral direction by a gap; and the gap is located proximal of the first cut point.

8. The medical device of claim 6, wherein:

at a second yaw orientation in the rotational yaw degree of freedom of the first blade with reference to the second blade, the first blade contacts the second blade at a second cut point distal of the first cut point; and the distal end portion of the first blade does not overlap the distal end portion of the second blade in the lateral direction.

9. The medical device of claim 6, wherein:

the first blade comprises a proximal portion located proximal of the pin;

the second blade comprises a proximal portion located proximal of the pin; and at the first yaw orientation of the first blade with reference to the second blade, the proximal portion of the first blade contacts the proximal portion of the second blade, the first and second blades are separated by a gap in the lateral direction, and the gap is located between the proximal portions of the first and second blades and the first cut point.

10. The medical device of claim 1, wherein:

the medical device further comprises a clevis and a spring;

the clevis comprises a clevis ear;

the pin extends from the blade support through the spring to the clevis ear; and the spring urges the blade support in the lateral direction toward the blade.

11. The medical device of claim 1, wherein:

the blade is a stamped metal blade.

12. The medical device of claim 1, wherein:

the outer portion of the bore is tapered outward in the lateral direction away from the blade.

13. A medical device comprising:

a blade support, a blade supported by the blade support, and a pin;

wherein the blade support comprises a bore;

wherein the bore comprises an inner portion oriented toward the blade, an outer portion oriented away from the blade, and a discontinuity at a boundary between the inner portion and the outer portion of the bore;

wherein the pin extends through the bore of the blade support;

wherein the blade support rotates about the pin in a yaw degree of freedom; and wherein a force on the blade in a lateral direction parallel to a longitudinal axis of the pin tilts the blade support in the lateral direction at the discontinuity of the bore.

14. The medical device of claim 13, wherein:

the blade is a first blade;

the first blade is flexible in the lateral direction;

in an unflexed state, the first blade has a first lateral curvature;

in a first flexed state, the first blade has a second lateral curvature straighter than the first lateral curvature;

in a second flexed state, the first blade has a third lateral curvature straighter than the second lateral curvature;

at a first cut point position on the first blade in relation to a second blade, the first blade is in the first flexed state or the second flexed state;

at a second cut point position on the first blade in relation to the second blade, the first blade is in a third flexed state; and the blade support tilts at the discontinuity of the bore as the first blade rotates to cut from the first cut point position to the second cut point position.

15. The medical device of claim 13, wherein:

the blade support comprises an inner support portion oriented toward the blade and an outer support portion oriented away from the blade;

the inner support portion of the blade support supports the blade;

the outer support portion of the blade support comprises an actuating cable groove; and

a solid plane defined by the actuating cable groove intersects the inner portion of the bore such that tension on an actuating cable in the actuating cable groove does not cause the blade support to tilt at the discontinuity of the bore.

16. The medical device of claim 13, wherein:

the medical device further comprises a cable;

the blade support comprises an inner support portion oriented toward the blade and an outer support portion oriented away from the blade;

the inner support portion of the blade support supports the blade;

the outer support portion of the blade support comprises a cable groove;

the cable is positioned in the cable groove;

a tension on the cable urges the blade support to rotate in the yaw degree of freedom; and the cable groove is positioned such that the tension on the cable does not cause the blade support to tilt at the discontinuity of the bore.

17. The medical device of claim 13, wherein:

contact between the outer portion of the bore and the pin limits tilting of the blade support at the discontinuity of the bore.

18. The medical device of claim 13, wherein:

the blade is a first blade and comprises a distal end portion;

the medical device further comprises a second blade, the second blade rotates about the pin, and the second blade comprises a distal end portion; and at a first yaw orientation of the first blade with reference to the second blade, the first blade contacts the second blade at a first cut point proximal of the distal end portion of the first blade, and the distal end portion of the first blade does not extend beyond the distal end portion of the second blade in the lateral direction.

19. The medical device of claim 18, wherein:

at the first yaw orientation of the first blade with reference to the second blade, the first blade and the second blade are separated by a gap in the lateral direction; and the gap is located proximal of the first cut point.

20. The medical device of claim 18, wherein:

at a second yaw orientation of the first blade with reference to the second blade, the first blade contacts the second blade at a second cut point distal of the first cut point; and the distal end portion of the first blade does not extend beyond the distal end portion of the second blade in lateral direction.

21. The medical device of claim 18, wherein:

the first blade comprises a proximal portion located proximal of the pin;

the second blade comprises a proximal portion located proximal of the pin; and at the first yaw orientation of the first blade with reference to the second blade, the proximal portion of the first blade contacts the proximal portion of the second blade, the first and second blades are separated by a gap in the lateral direction, and the gap is located between the proximal portions of the first and second blades and the first cut point.

22. The medical device of claim 13, wherein:

the medical device further comprises a clevis and a spring;

the clevis comprises a clevis ear;

the pin extends from the blade support through the spring to the clevis ear; and the spring urges the blade support in a direction toward the blade.

23. The medical device of claim 13, wherein:

the blade is a stamped metal blade.

24. The medical device of claim 13, wherein:

the outer portion of the bore is tapered.

25. A medical device comprising:

a blade support, a blade supported by the blade support, and a pin;

wherein the blade support comprises a bore;

wherein the bore comprises an inner portion oriented toward the blade, an outer portion oriented away from the blade, and a discontinuity at a boundary between the inner portion and the outer portion of the bore;

wherein the pin extends through the bore of the blade support;

wherein the pin includes a first end and a second end opposite the first end;

wherein a longitudinal axis of the pin is defined between the first and second ends of the pin, a lateral direction is defined as a direction parallel to the longitudinal axis of the pin, and a rotational yaw degree of freedom is defined about the pin; and wherein the blade support rotates about the pin in the rotational yaw degree of freedom, contacts the pin at the discontinuity of the bore, and a distal segment of the inner portion tilts away from the longitudinal axis of the pin at the discontinuity of the bore in response to a force applied in the lateral direction.

* * * * *